US012778485B2

(12) United States Patent
Shachar

(10) Patent No.: US 12,778,485 B2
(45) Date of Patent: Nov. 3, 2026

(54) USE OF LOCAL AMPLIFIERS AND A HUYGENS SENSOR ARRAY IN MEASURING BIOELECTRICAL SIGNALS AND CLINICAL APPLICATIONS THEREOF

(71) Applicant: Neurokinesis Corp., Inglewood, CA (US)

(72) Inventor: Josh Shachar, Santa Monica, CA (US)

(73) Assignee: Neuro-Kinesis Corporation, Inglewood, CA (US)

( * ) Notice: Subject to any disclaimer, the term of this patent is extended or adjusted under 35 U.S.C. 154(b) by 211 days.

(21) Appl. No.: 18/188,980

(22) PCT Filed: Aug. 9, 2022

(86) PCT No.: PCT/US2022/039798

§ 371 (c)(1),
(2) Date: Mar. 23, 2023

(87) PCT Pub. No.: WO2023/038748

PCT Pub. Date: Mar. 16, 2023

(65) Prior Publication Data

US 2024/0197235 A1 Jun. 20, 2024

Related U.S. Application Data

(63) Continuation-in-part of application No. PCT/US2022/030399, filed on May 20, 2022, which (Continued)

(51) Int. Cl.
*A61B 5/367* (2021.01)
*A61B 5/00* (2006.01)

(Continued)

(52) U.S. Cl.
CPC ............ *A61B 5/367* (2021.01); *A61B 5/0006* (2013.01); *A61B 5/0017* (2013.01); *A61B 5/201* (2013.01);

(Continued)

(58) Field of Classification Search
None
See application file for complete search history.

(56) References Cited

U.S. PATENT DOCUMENTS 5,769,791 A 6/1998 Benaron
6,546,270 B1 4/2003 Goldin (Continued)

OTHER PUBLICATIONS

Josh Schachar, Inventor Scientist Enterpreneur, obtained from https://joshshachar.com/wp-content/uploads/2021/10/jshachar-cv.pdf on Dec. 19, 2025 (Year: 2025).*

(Continued)

*Primary Examiner* — Manolis Pahakis
(74) *Attorney, Agent, or Firm* — Kirton McConkie; Brian Tucker

(57) ABSTRACT

With respect to the methodology of using the Huygens sensing array, the invention includes an improvement in a method of sensing biopotentials in tissue including the steps of: providing a Huygens sensor array, and sensing a native electrical biopotential signal using at least one electrode on a catheter with an amplifier circuit placed on the inner surface of the at least one electrode in the Huygens sensor array to generate a well-formed waveform of the biopotential showing clear electrical properties indicative of the tissue with a SFDR of at least 24.9 dB and SNR of at least −13 dB. In one embodiment the tissue is cardiac tissue and the biopotential signal sensed by the Huygens sensing array is a native cardiac waveform. In one embodiment the sensed biopotential signal is a manifestation of underlying electro- (Continued)

chemical activity sensed by the Huygens sensing array of a biological substrate corresponding to the tissue.

1 Claim, 11 Drawing Sheets

Related U.S. Application Data is a continuation of application No. 17/468,460, filed on Sep. 7, 2021, now Pat. No. 12,279,876.

(51) Int. Cl.
*A61B 5/20* (2006.01)
*A61B 5/287* (2021.01)
*A61B 5/294* (2021.01)
*A61B 5/308* (2021.01)
*A61B 5/35* (2021.01)
*A61B 5/388* (2021.01)
*G16H 40/63* (2018.01)

(52) U.S. Cl.
CPC .............. *A61B 5/287* (2021.01); *A61B 5/294* (2021.01); *A61B 5/308* (2021.01); *A61B 5/35* (2021.01); *A61B 5/388* (2021.01); *A61B 5/4836* (2013.01); *A61B 5/6852* (2013.01); *A61B 5/686* (2013.01); *A61B 5/7203* (2013.01); *A61B 5/7271* (2013.01); *A61B 5/742* (2013.01); *G16H 40/63* (2018.01); *A61B 2560/0468* (2013.01); *A61B 2562/0209* (2013.01); *A61B 2562/146* (2013.01); *A61B 2562/166* (2013.01)

(56) References Cited

U.S. PATENT DOCUMENTS 6,569,160 B1 5/2003 Goldin
7,769,427 B2 * 8/2010 Shachar ................. A61B 34/20 606/1
7,869,854 B2 * 1/2011 Shachar ................. A61B 34/73 600/374
9,220,425 B2 12/2015 Shachar
9,381,063 B2 * 7/2016 Gang ..................... A61B 34/73
11,844,912 B2 12/2023 Alsheikh
12,279,876 B2 * 4/2025 Shachar ................. A61B 5/388
2003/0100938 A1 * 5/2003 Rubenchik ............... A61N 1/40 623/1.1
2004/0019447 A1 * 1/2004 Shachar ................. A61B 17/22 702/115
2006/0116634 A1 * 6/2006 Shachar ................... A61B 5/06 604/95.01
2007/0156128 A1 7/2007 Jimenez
2007/0185404 A1 8/2007 Hauck et al.
2007/0197891 A1 * 8/2007 Shachar ................... A61B 5/33 600/374
2007/0276286 A1 11/2007 Miller
2009/0248014 A1 * 10/2009 Shachar ................. A61B 5/318 606/41
2010/0160737 A1 * 6/2010 Shachar ................. A61B 17/02 600/202
2014/0018792 A1 * 1/2014 Gang ................. A61B 18/1492 606/41
2015/0313501 A1 * 11/2015 Shachar ................. A61B 5/302 600/374
2018/0303414 A1 10/2018 Toth
2020/0375541 A1 * 12/2020 Shachar ............... A61B 5/7435
2021/0181192 A1 * 6/2021 Shachar ........... G01N 33/54333
2021/0212764 A1 * 7/2021 Eskandar .................. H01S 1/02
2022/0047202 A1 * 2/2022 Shachar ................. A61B 5/686
2024/0197235 A1 * 6/2024 Shachar ................. A61B 34/30
2025/0383347 A1 * 12/2025 Preston ............ G01N 33/54326

OTHER PUBLICATIONS

Shachar, Josh Yehoshua, "The Use of Local Amplifier and MOSFET Sensor Array in Measuring Bioelectric Signals and Its Clinical Application," research paper, Jan. 1, 2018, <https://joshshachar.com/wp-content/uploads/2021/07/jshachar-introduction-to-mosf et-technology-research-paper.pdf>.
European Patent Office, Communication pursuant to Rule 164(1) EPC and European Search Report, Jun. 30, 2025.
European Patent Office, Extended European Search Report, Oct. 10, 2024.

* cited by examiner (A)

(B)

USE OF LOCAL AMPLIFIERS AND A HUYGENS SENSOR ARRAY IN MEASURING BIOELECTRICAL SIGNALS AND CLINICAL APPLICATIONS THEREOF

RELATED APPLICATIONS

This application is a continuation in part and claims priority to, and the benefit of the earlier filing date of ROBOTICALLY CONTROLLED ELECTROPHYSIOLOGY CATHETER WITH CLOSED LOOP CONTROL, PCT Pat. Appl. PCT/US22/30399, filed May 20, 2022, incorporated herein by reference and A CATHETER FOR CARDIAC AND RENAL NERVE SENSING AND MEDIATION, U.S. patent application Ser. No. 17/468,460, filed Sep. 7, 2021 and granted as U.S. Pat. No. 12,279,876, incorporated herein by reference pursuant to 35 USC 120.

BACKGROUND

Field of the Technology

The invention relates to the field of electrophysiological mapping methods using a catheter with capabilities of measuring impedance and local native biometric signals and employing such signals with a method that identify a "phase singularity" within the electroanatomical space and its dynamics.

Description of the Prior Art

Tissue electrode interface is common to all forms of biopotential recording (e.g., ECG, EMG, EEG) and functional electrical stimulation (e.g., pacemaker, cochlear implant, deep brain stimulation). The disclosed technology employs local amplification by means of a Huygens™ catheter (a trademark of Neurokinesis Corp., Inglewood, California) at the bioelectric site, which demonstrates substantial reduction in signal-to-noise ratio (SNR), while improving spurious-free dynamic range (SFDR). Details of the Huygens catheter as provided by U.S. Pat. Applications (PHA3.PAU.57A) ROBOTICALLY CONTROLLED ELECTROPHYSIOLOGY CATHETER WITH CLOSED LOOP CONTROL, PCT Pat. Appl. PCT/US22/30399, incorporated herein by reference and A CATHETER FOR CARDIAC AND RENAL NERVE SENSING AND MEDIATION, U.S. patent application Ser. No. 17/468,460, filed Sep. 7, 2021, incorporated herein by reference.

The problem to be solved is how to identify the arrhythmogenic cause of fibrillation, which the Huygens catheter is capable of doing by measuring the impedance value of the tissue, in order to create an actual measure of the anisotropic wave propagation.

The current art of electrophysiology mapping techniques and its applications is detailed and described by a review paper by Li et al in Physiol., 21 Jul. 2020 "Standardizing Single-Frame Phase Singularity Identification Algorithms and Parameters in Phase Mapping During Human Atrial Fibrillation", stating that "Recent investigations failed to reproduce the positive rotor-guided ablation outcomes shown by initial studies for treating persistent atrial fibrillation (persAF). Phase singularity (PS) is an important feature for AF driver detection, but algorithms for automated PS identification differ."

The authors conclude that "In the present study, we demonstrate that automated Phase Singularity detection—and consequently persAF ablation target identification—vary significantly for the same individual, depending on the method being used and parameters being applied. The present study represents a step toward a unified definition/algorithm of phase-derived PS detection with standardized gradient and spatial thresholds, which is essential to allow objective comparisons of outcomes of rotor ablation for persAF therapy among different research/clinical centers."

As noted by Li et al in a comprehensive monograph noted above, in which the authors' process of obtaining the spatial coordinates of the PS is based on mathematical-statistical methods where a computational algorithm is capable of sorting the locus of the rotor generator focal position of the electrical activity by employing a "2048-channel virtual electrogram (VEGM) and electrocardiogram signals were collected for 30 s from 10 patients undergoing persAF ablation. QRST-subtraction was performed and virtual electrogram EGMs were processed using sinusoidal wavelet reconstruction. The phase was obtained using Hilbert transform. PSs were detected using four algorithms: (1) two dimensional image processing based and neighbor-indexing algorithm; (2) three dimensional neighbor-indexing algorithm; (3) two dimensional kernel convolutional algorithm estimating topological charge; and (4) topological charge estimation on a three dimensional mesh. PS annotations were compared using a structural similarity index (SSIM) and Pearson's correlation coefficient (CORR). Optimized parameters to improve detection accuracy were found for all four algorithms using $F_\beta$ score and 10-fold cross-validation compared with manual annotation. Local clustering with density-based spatial clustering of applications with noise was proposed to improve algorithms 3 and 4."

It is clear from the four methods proposed and its data acquisition modes by which the identification of the Phase Singularity is obtained are highly depended on the complex and subjective selections of parameters which in turn are subjected to the "$F_\beta$ score" analysis, due to assignments of non-symmetric preferences of some of the parameters relative value in assessing the locus of the Phase Singularity.

The differentiation between atrial flutter and atrial fibrillation in a location where such phenomenon occurs is another source of error which add to the identification of Phase Singularity.

Our application teaches an apparatus and method for the identification of the locus associated with atrial fibrillation by the use of the Huygens catheter and its ability to measure with near real-time the impedance as well as the tissue potential and thereby solving the variables in the algorithm we employ titled "Signal Anisotropy, Modeling Bipotential Activity with the Poynting Energy Vector (PEV)" described below. This technique is not available anywhere in the leading theories of the underlying mechanisms which defines the difference between a phenomenon called "atrial flutter" and one called "atrial fibrillation". While flutter is marked by the gap associated with scar and fibrotic tissue, which inhibits the transport of the ionic charge of the wave propagation along the conduction path, fibrillation is a phenomenon physically correlated with a physical phenomenon described as "rotors".

In summary, the differentiation between flutter and fibrillation due to the anisotropic behavior of the wavefront dynamics, is the regeneration of the fibrillating foci, where the front of the wave and the tail of the wave are spiraling, while flutter is a simple fractionated electrogram, where the tail is just an end represented by a capacitance delay. In fibrillation the focus of the energy is a generator where its equivalent circuit representation is a variable resistor. The main difference between fibrillation and flutter is the gap or the nature of the encroachment of the front into the tail: the gap is fully excitable and quite large in flutter, whereas it is smaller and partially excitable in AF, because of the intermingled front and tail. A detailed study of the physics as well as the physiology of cardiac cell mechanism is articulated by Sandeep V. Pandit and José Jalife "Rotors and the Dynamics of Cardiac Fibrillation"

The Huygens catheter is the only tool in existence today that can measure both the DC potential as well as the tissue contact impedance (conductivity) for the same tissue area. This enables us to employ the Maxwell second set of time-varying equations, by substituting the magnetic energy vector (MEV) with the Poynting Energy Vector (P) where we substitute the B terms with the impedance measured value Z. The impedance Z is measured nearly simultaneously with the measurement of the electric potential E of the heart wave using separately sensing electrodes on the Huygens catheter and sensing and signal processing circuitry. Since the E and B fields are in temporal quadrature, their strengths cannot be simultaneously measured, but they can be measured in near simultaneity since the sample rate of the Huygens catheter is of the order of 1 kHz compared to the 1 Hz beat rate of the heart and the heart wave. Thus, an approximate value of the Poynting vector, E×B, can be measured at any given time, substituting the measured impedance Z for a computed value for B. This is a derivation that was never described in the literature of the causal relationship between conduction path and fibrillation. The mechanism used to describe fibrillation is associated with the theory defined under the heading "phase singularity" whereby the computer on the back-end of the Huygens catheter performs a phase study separating normal tissue from fibrotic/scar tissue. The disclosed technique using the Huygens catheter with the algorithm provided using Maxwell's equations distinguishes the invention from the existing art.

BRIEF SUMMARY

The methodology of the illustrated embodiments of the apparatus of the invention is demonstrated by comparing the sensing a native QRS signal of the heart, generated and transmitted through a conventional decapolar catheter, where one pair of electrodes is configured to amplify the native heart signal with an analog-to-digital converter (ADC) and amplifier combination. An identical QRS signal is transmitted through a second pair of electrodes where the electrodes were modified to incorporate a Huygens™ sensor array in the form of amplifier circuit placed on the inner surface of the electrode(s).

The measurement results of the conventional first electrode pair is compared with the results of a computer simulation, and compared with the electrode—Huygens™ sensor array output. The post-amplified cardiac path (using standard electrode technology) is measured to show that the reference signal is nearly imperceptible due to noise degradation. Spurious-free dynamic range (SFDR) is defined as the strength ratio of the fundamental signal to the strongest spurious signal in the output. The final result shows a spurious-free dynamic range (SFDR) of 9.3 dB with a signal-to-noise ratio (SNR) of −50 dB. In contrast, when the same signal is run through the pre-amplified Huygens™ cardiac path, it is shown to be well-formed and the cardiac properties are clear, and the final result shows a vastly improved SFDR of 24.9 dB and SNR of only −13 dB.

The increase in signal quality of the Huygens™ sensor array as a local amplifier creates a new standard of quality in measuring bioelectric signals and well outperforms the current electrode technology.

Electrograms are a manifestation of the underlying electrochemical activity of a biological substrate, and the attempt to functionalize and fashion a diagnostic value upon such graphical representation must first assume that the fidelity of the measured native signal is a true representation of an "energetic event," as energy with its vectorial direction and magnitude is the appropriate parameters for a diagnostic measure. The question of focus becomes: "Can the electrogram path represent the underlying substrate composition?"

What we demonstrate below is centered on the ability of a measuring apparatus employing a catheter fitted with an electrode technology (i.e. at the site of biopotential activity) to capture the signal in its native form. The current technology with its post-processing algorithms distorts and masks the true nature of the complex wavefronts and "washes out" substantial clinical details, resulting in a non-unique diagnosis as to the underlying nature of the disease mechanism.

Conventional measuring apparatus employing electrode(s) with an amplifier at the distal end of the catheter shaft is compared below with use of a local amplifier in a Huygens™ sensor array, which array enables an accurate "one-to-one" correlation while forming an electrophysiological map. The biopotential measurement using a Huygens sensor array substantially improves the representation of the energy contents on the spatial and time domains of the complex cardiac waveform, leading to a recursive relationship between the graphical representation and the underlying biopotential substrate which causes such electrical activity.

Conventional electrode technology utilizing post-processing algorithms has tried with limited success to resolve the diagnostic discrepancy between the bottom-up causal representation (i.e., substrate mapping) and the top-down causal description of the underlying mechanism generating the pathology observed. This limitation is cited in many clinical publications and is most clearly evident in the diagnosis and treatment of complex arrhythmias.

As indicated by the current status of clinical results, there are presently at least two approaches to determining the underlying mechanism for modeling a disease: 1) the reductionist approach, which advocates "substrate mapping" correlations with ECG, (See Volkmer et al. "Substrate Mapping vs. Tachycardia Mapping using CARTO in Patients with Coronary Artery Disease and Ventricular Tachycardia: Impact on Outcome of Catheter Ablation", Oxford Journals Medicine EP Europace Volume 8, Issue 11 Pp. 968-976) and 2) the anatomical approach, which supports "anatomical mapping." (Deepak Bhakta et al., "Principles of Electroanatomic Mapping", Electrophysiol J. 2008 January-March; 8(1): 32-50). In contrast, the discussion should be centered on the nature of the measuring apparatus's fidelity and the establishment of a "standard model" in electrophysiology (EP) while employing an apparatus which will enable both methodologies to form a uniform mapping manifold. A standard model would provide for a common method of assessing the data and its "elementary building blocks," which will improve not only the diagnostic and mapping procedures but also the therapeutic outcome.

One of the foremost goals of the EP community is to develop a comprehensive mapping technique to characterize the global dynamics of wavefront activation. This must, first, be anchored in a bottom-up consensus where the elementary building blocks are accepted and agreed upon metrically, and whereby the cellular etiology and its electrical counterparts—e.g., dielectric (κ) and conductivity (σ)—are defined. The complexity and inter-relationships of the "avalanche" dynamics which are translated through the myocardial space, due to ionic potential on the spatial as well as time domains, can be resolved by the use of heuristic top-down causal theory, when employing the local amplifier Huygens™ sensor array.

With respect to the methodology of using the Huygens sensing array, the illustrated embodiments of the invention include an improvement in a method of sensing biopotentials in tissue including the steps of: providing a Huygens sensor array; and sensing a native electrical biopotential signal using at least one electrode on a catheter with an amplifier circuit placed on the inner surface of the at least one electrode in the Huygens sensor array to generate a well-formed waveform of the biopotential showing clear electrical properties indicative of the tissue with a SFDR of at least 24.9 dB and SNR of at least −13 dB.

In one embodiment the tissue is cardiac tissue and the biopotential signal sensed by the Huygens sensing array is a native cardiac waveform.

In one embodiment the sensed biopotential signal is a manifestation of underlying electrochemical activity sensed by the Huygens sensing array of a biological substrate corresponding to the tissue.

In one embodiment, the manifestation of underlying electrochemical activity of a biological substrate corresponding to the tissue is an energetic event characterized by vectorial direction and magnitude sensed by the Huygens sensing array.

In one embodiment, the manifestation of underlying electrochemical activity of a biological substrate sensed by the Huygens sensing array corresponding to the tissue is a representation of the underlying substrate composition of the tissue.

In one embodiment, the manifestation of underlying electrochemical activity of a biological substrate corresponding to the tissue is a biopotential measurement using the Huygens sensor array to generate a representation of the energy contents on the spatial and time domains of a complex cardiac waveform, leading to a recursive relationship between a graphical representation of the cardiac waveform and an underlying biopotential substrate which is a source of the cardiac waveform.

In one embodiment, the manifestation of underlying electrochemical activity of a biological substrate corresponding to the tissue includes a mapping which characterizes global dynamics of cardiac wavefront activation based on cellular etiology and corresponding dielectric (κ) and conductivity (σ) characteristics of the tissue representing complex inter-relationships of avalanche dynamics translated through a measured myocardial space arising from spatial and temporal ionic potentials measured by a local amplifier Huygens sensor array.

In one embodiment, sensing a native electrical biopotential signal using at least one electrode on a catheter with an amplifier circuit placed on the inner surface of the at least one electrode in the Huygens sensor array includes sensing by performing impedance spectroscopy.

In one embodiment, sensing a native electrical biopotential signal using at least one electrode on a catheter with an amplifier circuit placed on the inner surface of the at least one electrode in the Huygens sensor array includes sensing an energetic event represented by the native electrical biopotential signal in the tissue by relating its inherent characteristics of time, magnitude and direction without post-processing of the native electrical biopotential signal.

In one embodiment, sensing a native electrical biopotential signal using at least one electrode on a catheter with an amplifier circuit placed on the inner surface of the at least one electrode in the Huygens sensor array includes sensing the native electrical potential signal using a local amplifier which acts as variable resistor with an on-site electrical ground, which ground is not subject to noise pickup to improve signal-to-noise ratio (SNR), spurious-free dynamic range (SFDR), signal fidelity, sampling rate, bandwidth, and differentiation of far-field from near-field components of the sensed native electrical potential signal.

In one embodiment, the method further includes the step of using the Huygens sensor array with mapping stations without alteration thereof.

In one embodiment, the method further includes the step of detecting an energetic event in the tissue using the Huygens™ sensor array to generate an ensemble vector map to characterize spatiotemporal organization of cardiac fibrillation.

In one embodiment, the method further includes the step of using the Huygens™ sensor array with a predetermined geometric configuration, including bipolar, quadripolar, decapolar, or any array with 64 or more electrodes, to enable a plurality of electrodes to simultaneously capture a complex electro-potential energetic event, with an improved SNR and sampling rate commensurable with a bandwidth and accuracy in a spatio-temporal domain.

In one embodiment, the method further includes the step of capturing bioelectric potential data, which is anchored in a measurement that reveals the physical nature of a biological substrate's electrical properties of underlying tissue to allow for interpretation of the phenomenological expression of an electrogram (EGM) and its graphical representation in the context of an energetic event, based on the dielectric (κ) and conductivity (σ) measurements of underlying tissue.

In one embodiment, the method further includes the step of connecting an electroanatomic map with an inherent physical relationship between an energy transfer function and its causal dependency on a substrate tissue as represented by an electrogram by using a Huygens™ sensor array for conducting an electrophysiological study.

In one embodiment, the method further includes the step of connecting phenomenological data with clinical observation so that electrical properties of a conduction path within a cardiac substrate and its etiological constituents are correlated without the need to create a causal dependency.

In one embodiment, the method further includes the step of synchronously capturing spatial and temporal complexity of an energetic cardiac event using the Huygens™ sensor array to mimic underlying cardiac dynamics by localizing and precisely identifying arrhythmogenic substrates removed from fluoroscopic landmarks and lacking characteristic electrogram patterns.

In one embodiment, the method further includes the step of generating a cardiac map comprised of superimposed electric and energy wave maps by converging the electric heart vector with the magnetic heart vector by computing an impedance (Z) value generated from the substrate.

In one embodiment, the method further includes the step of simultaneously localizing and mapping (SLAM) magnetic fields during a cellular activation sequence to uncover a magnetic heart vector (MHV) by computing a vector derived from Maxwell's equations by deriving the Poynting energy vector PEV from a measured impedance vector (Z) sensed using the Huygens™ sensor array with a computational algorithm.

In one embodiment, the method further includes the step of measuring a phase difference, β, between PEV and EHV to infer features of anisotropy in a myocardium.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 4 shows three snapshots in upper row A of the progression of two wavefronts initiated in a medium with 10% fibrosis and with a coupling interval of 321 ms between them; and three snapshots in lower row B of the progression of two wavefronts initiated in a medium with 30% fibrosis and with a coupling interval of 320 ms between them FIG. 5 on the left panel is a color electrogram showing precise lesion placement which is required for treatment of arrhythmias for which ablation shown in the right panel are most effective (e.g., accessory pathways, atrioventricular nodal re-entry tachycardia [AVNRT]) and which are largely anatomically based or directed substrates.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 12:
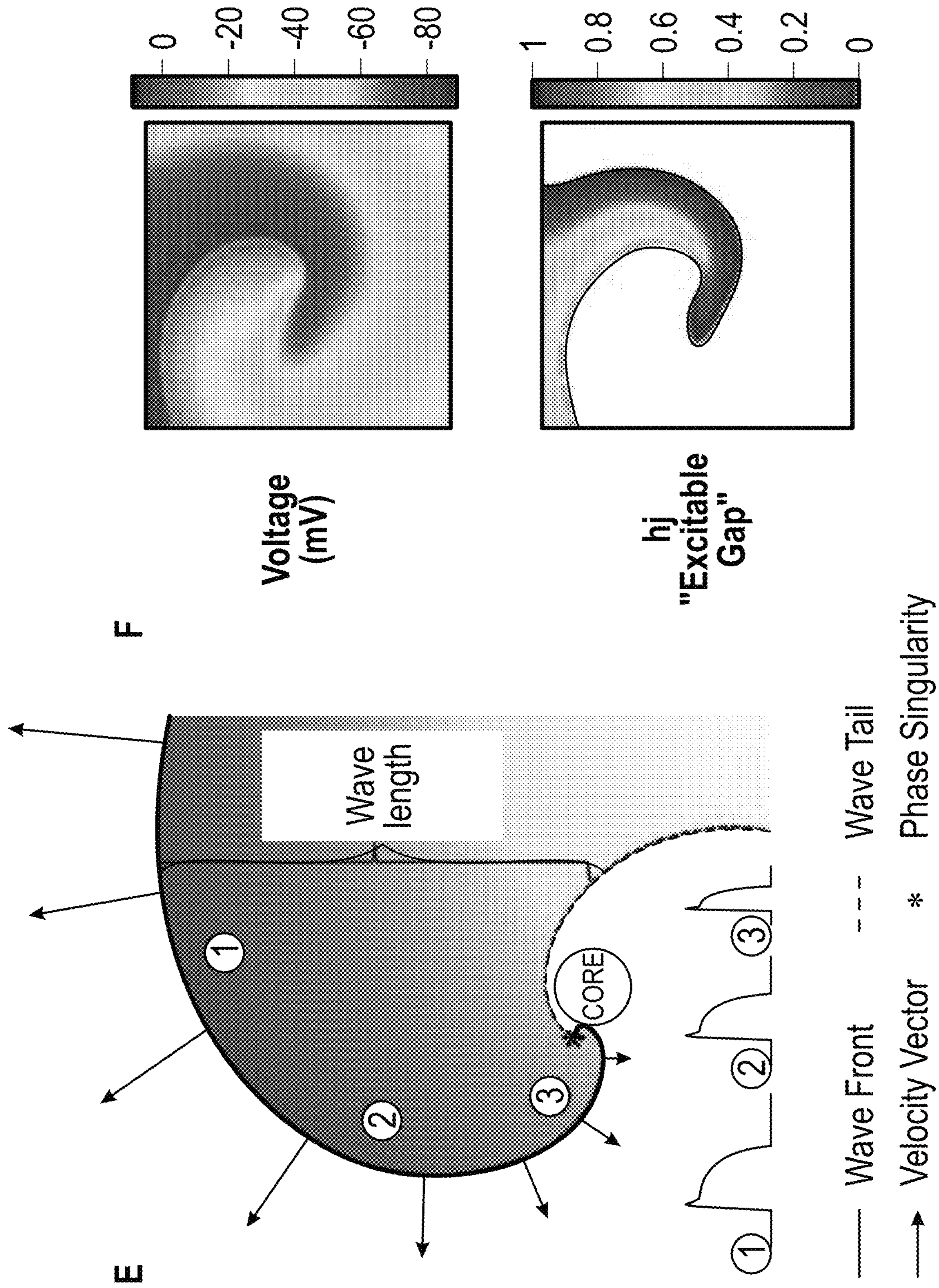
FIG. 12 is a diagram illustrated some basic concepts of rotors and spirals in heart waves.

Determining optimal treatment strategies for complex arrhymogenesis in AF is conducted by the lack of consensus regarding the mechanisms causing AF. The studies report different mechanisms for AF, ranging from hierarchical drivers to multiple activation modes. Differences in assessment of AF mechanism are likely due to the different investigational tools employed, scaling and the population variabilities used in the studies. The Huygens catheter and the proposed algorithm employed enable a uniform derivation of the focal targeted locus for such application, where the ability of the system and method is to create a uniform data acquisition of the cardiac dynamics, simplicity in the operation of yielding such a target as a rotor initiator and ultimately the ability of the therapeutic application of ablation procedure to terminate the arrhymogenic cause for persistent AF. In the leftmost side of FIG. 12 is a diagram which is a snapshot of a spiral cardiac wave: electrotonic effects of the core decrease conduction velocity (arrows), and action potential duration (representative examples shown from positions 1, 2, and 3), and wavelength (the distance from the wavefront [black line] to the wave tail [dashed line]). Conduction velocity (CV) decreases and wavefront curvature becomes more pronounced, near the rotor, which is a phase singularity at the point where the wavefront and the wave tail meet (shown in FIG. 12 by an asterisk*). In the rightmost side of FIG. 12 is a depiction of a computer simulation of cardiac wave reentry. On the top position is a snapshot of the transmembrane voltage distribution during simulated reentry in chronic atrial fibrillation (AF) conditions in a two-dimensional sheet incorporating human atrial ionic math models. In the bottom position is a snapshot of inactivation variables of sodium current, "high" during reentry. Greater detail concerning spiral and reentry waveforms is given in Sandeep V. Pandit, José Jalife, "Rotors and the Dynamics of Cardiac Fibrillation", *Circ Res.* 2013; 112:849-862 (2012).

The Huygens Solution

There is a relationship between the quality of the measuring apparatus and its ability to resolve the signal accuracy and its signal-to-noise ratio (SNR), as well as the fidelity and repeatability of the data generated. This disclosure will address the shortcoming of the current electrode technology and the improvement provided by the use of a local amplifier with its embodiments, as a solution to the limitations noted by the existing art.

Current attempts to resolve the myriad of above-mentioned issues utilize the method of post-production processing which employs, subsequent to the native measurement, algorithmic tools such as a Fast Fourier Transform (FFT) technique or recursive methods. As a result, the EP community is currently faced with a state of affairs as described and exemplified in the published clinical journals cited below.

The Huygens™ technology utilizes impedance spectroscopy at the event site of the biopotential signal. Just as microscopy provided for magnification which produced a novel view of matter at orders of magnitude which were previously imperceptible, impedance spectroscopy provides an additional tool for an electrophysiologist that can resolve the distortions caused by the noise characteristic of the current art to allow study of the inherent relationship between the substrate and its corresponding electrical activity.

The use of a local amplifier in the Huygens™ sensor array is a solution to shortcomings of the prior art. That the native bioelectrical signal in the form of ionic electrochemical avalanche dynamics is addressed by locating the preamplifier (Huygens™) element adjacent to the measurement site. That measurement is capable of "mining" the "energetic event" by relating its inherent characteristics of time, magnitude and direction without post-processing of the native signal, as in the prior art. These aims are achieved by employing a local pre-amplification with the characteristic signal fidelity as demonstrated below.

Figure 11:
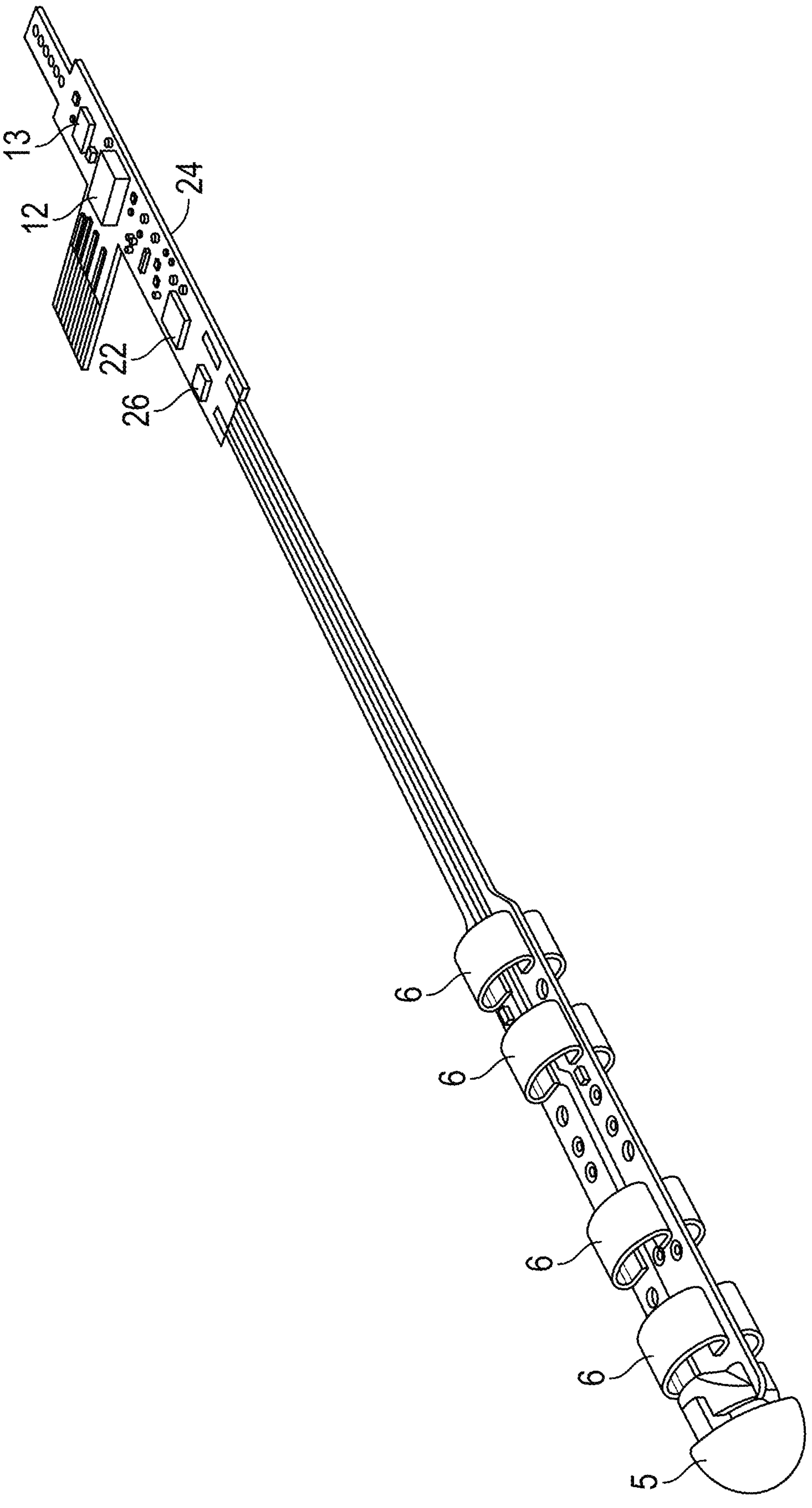
FIG. 11 is a perspective view of a nonencapsulated Huygens catheter tip showing the tip electrodes, a flexible length of printed circuit board coupled to the electrodes and a proximal portion of the circuit board carrying all of the tip electronics for providing local amplification and digitization of the electrode signals for transmission to a remote data processing station.

The shortcoming of the prior electrode technology is emphasized by comparison with the improvements provided by the disclosure, which is defined by the term "Huygens™." Simply stated, a local amplifier acts as variable resistor. Its on-site electrical ground is not subject to noise pickup from the 5-ft. antenna/conductor, which the catheter shaft forms, and which acts as a receiver/carrier for equipment located in the operating room with EMI frequencies ranging from 50-60 Hz to 5-10 kHz. FIG. 11 shows the tip of the Huygens catheter in which all amplification, signal sensing, and signal conditioning occurs in electronics provided at or on the catheter tip or at least proximate thereto. FIG. 11 is taken from FIG. 12 of incorporated patent application, U.S. patent application Ser. No. 17/468,460, where additional detail and disclosure of the Huygens catheter tip is provided. FIG. 11 shows that all of the sensing, amplification and signal processing circuitry, including digitization, related to the sensed electrode signals occurs at or proximate to the electrodes at or near the catheter tip. The disclosed approach of local amplification employs pre-amplification technology which substantially improves signal-to-noise ratio (SNR), spurious-free dynamic range—SFDR—signal fidelity, sampling rate, bandwidth, and differentiation of far-field from near-field components.

It can be appreciated that measuring small bioelectrical signals with the Huygens™ technology applies to a wide variety of medical applications. For example, electrophysiological maps can be created to establish accurate diagnostic maps which improve the subsequent therapeutic outcome. The electrical characteristics of Huygens™ can resolve many of the existing problems arising from the electrode technology interface, where the ratio of signal magnitude compared to the noise impairs the ability of the clinician to form an adequate and reliable diagnosis.

Conventional electrode technology is limited in providing uniform diagnostic metrics, and thus the clinical observations provided are oftentimes merely anecdotal indications. The Huygens™ sensor array, as a model for local pre-amplification supplements the current electrode technology to provide benefits by complementing the existing technology when incorporated therein. The current architecture of mapping apparatus such as CARTO™ or EnSite®, as well as their tool sets (e.g., catheters), need not be modified with respect to their generic metrics (e.g., bipolar, quadripolar, decapolar, balloon, basket), and are not altered since the Huygens™ amplifier and its associated circuitry is adopted within the existing catheter shaft. The Huygens™ technology can be seamlessly incorporated into the existing hardware of mapping stations and operator skills. The change would be essentially invisible to the user.

The Huygens Pre-Amplification Compared to Post-Amplification Methods

Figure 1:
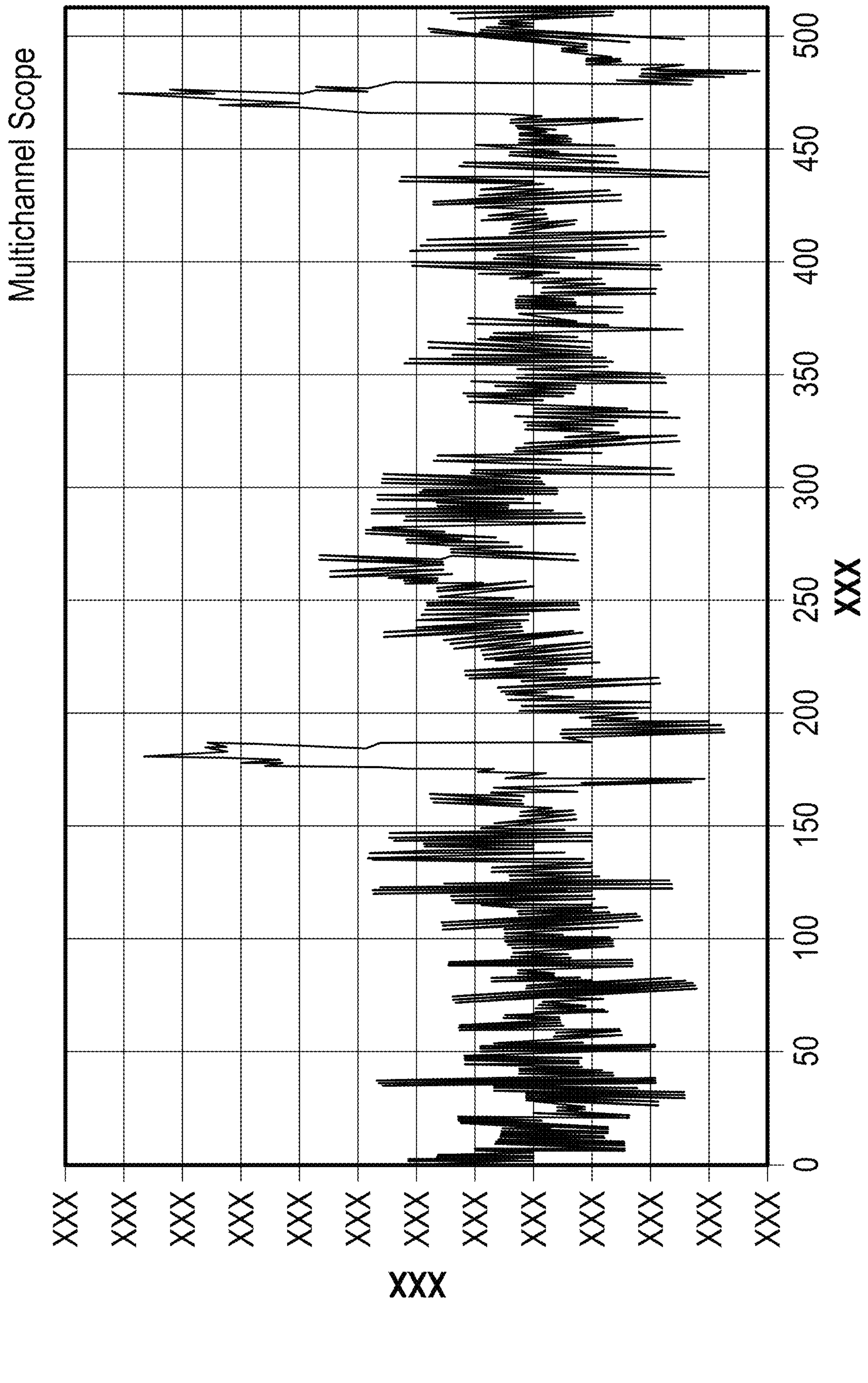
FIG. 1 is a wave trace of the voltage of a cardiac signal as a function of time in a post-amplified path which shows that the reference signal is nearly imperceptible at this level due to noise degradation.

Experimental application of the technology is discussed below to demonstrate a proof of concept and the superior performance of a Huygens™ sensor array in detecting bioelectric potentials in the circuit depicted in FIG. 1. A comparison of the local amplifier employing Huygens™ versus the remote amplifier was conducted.

Simulated cardiac (QRS) signals are generated by a programmable generator (Agilent Trueform Wave Generator, 33500B Series) and measured along two different signal paths, one employing a post-amplified (using current electrode technology) and the second channel containing a locally amplified Huygens™ sensor array. In the unamplified pathway, a conventional decapolar geometry catheter is post-amplified using ADC Pro computer software, simulating the current method of electrode technology. In the amplified pathway, the identical geometry and metric layout is employed using a common, single catheter shaft for both configurations, with the only difference being that the amplification now occurred at the site of the electrodes using the Huygens™ sensor array. Thus, the only variable measured was the fidelity of the simulated QRS, enabling a comparative evaluation of the resultant signals from each amplification method.

The signal is first attenuated to under 50 μV peak-to-peak by adding series attenuators to the input signal from conventional electrode technology with a total signal gain of 128. The post-amplified path is measured in FIG. 1 to show that the reference signal is nearly imperceptible at this level due to noise degradation. The final result shows a spurious-free dynamic range SFDR of 9.3 dB with a signal-to-noise ratio (SNR) of −50 dB.

Figure 2:
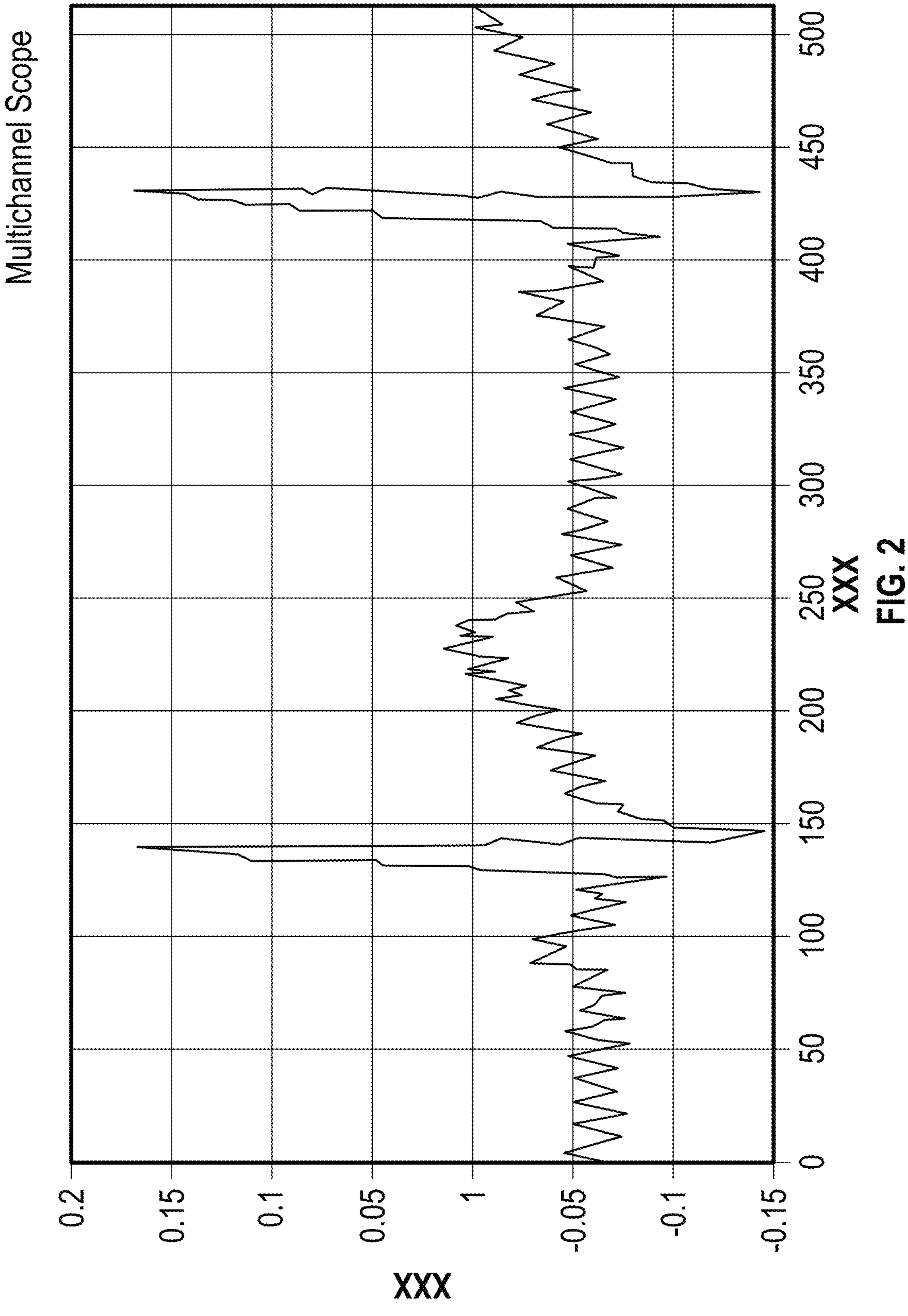
FIG. 2 is a wave trace of the voltage of the signal shown in FIG. 1 as a function of time after being run through the Huygens sensor array.
Figure 3:
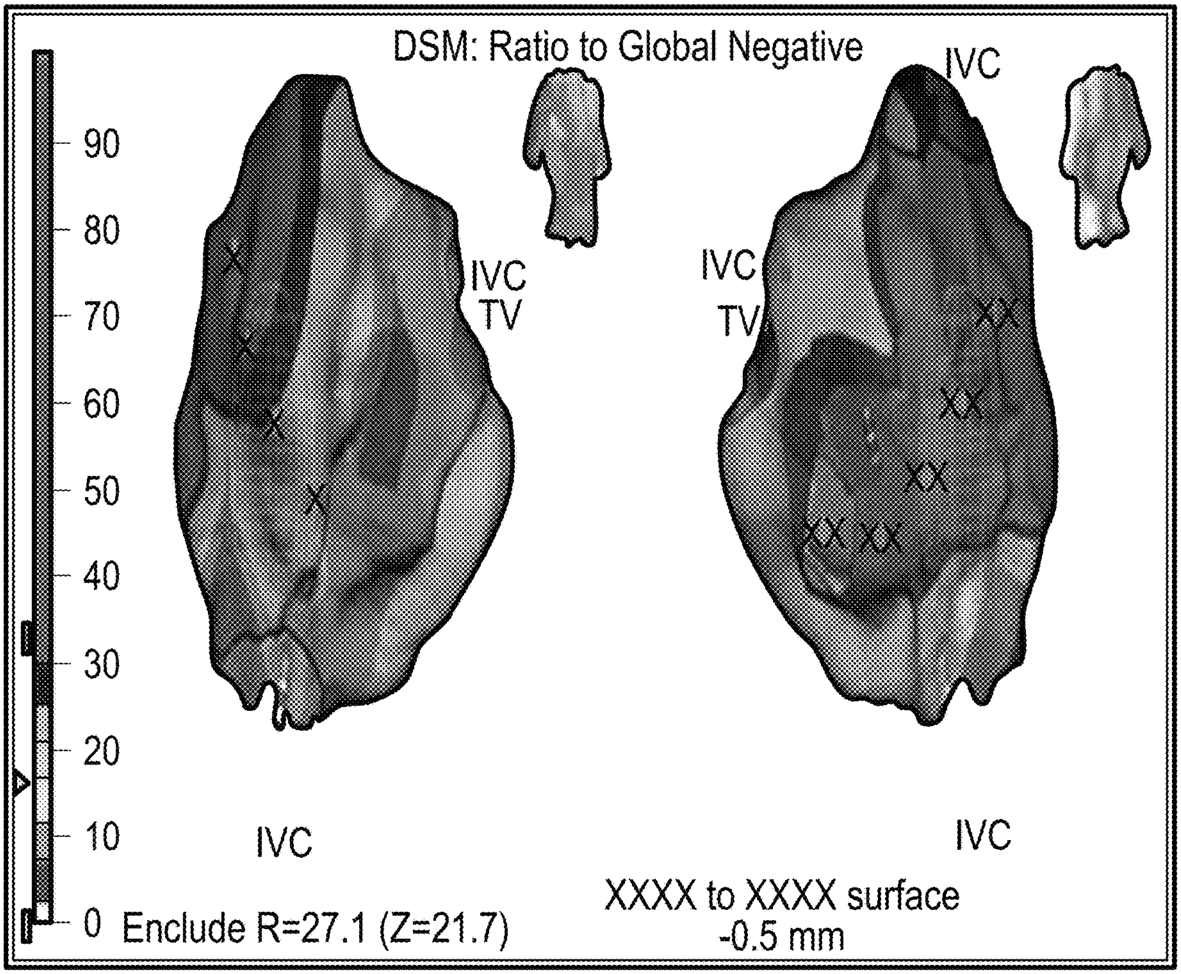
FIG. 3 is a color electroanatomic map with high fidelity and accuracy depicting a local electrogram with its native dynamics, its geometrical as well as its time domain specificity and further providing for reconstruction of the anatomical and the extrapolated etiological characteristics of the cellular matrix by employing the Huygens™ sensor array.

In contrast, when the same signal is run through the pre-amplified Huygens™ path as seen in FIG. 2, it is shown to be well-formed, and the cardiac properties are clear. Here, the total signal gain is only 100, with the location of the gain block having been moved from one end of the catheter to another and the final result shows a vastly improved SFDR of 24.9 dB and SNR of only −13 dB.

When the QRS-simulated signal is captured by the local amplifier at the site of the electrodes, linked to a local Huygens™ sensor, the result is substantially identical to the "pure" standard. The cardiac signal, replicated using Trueform™ waveform generator technology (a trademark of Keysight, Colorado Springs, Colorado), is then repeated while the amplifier is located at the distal end of the catheter connector with post-amplification. The signal quality is due to the pre-amplified embodiment of locating the measurement at the site of the signal source. These and other features relating to the use of Huygens™ inherent local ground with its variable resistor, matching the characteristics of the biopotential at the measurement site, are material characteristics of Huygens.

Clinical Observations Using the Huygens Sensor Array

Figure 9:
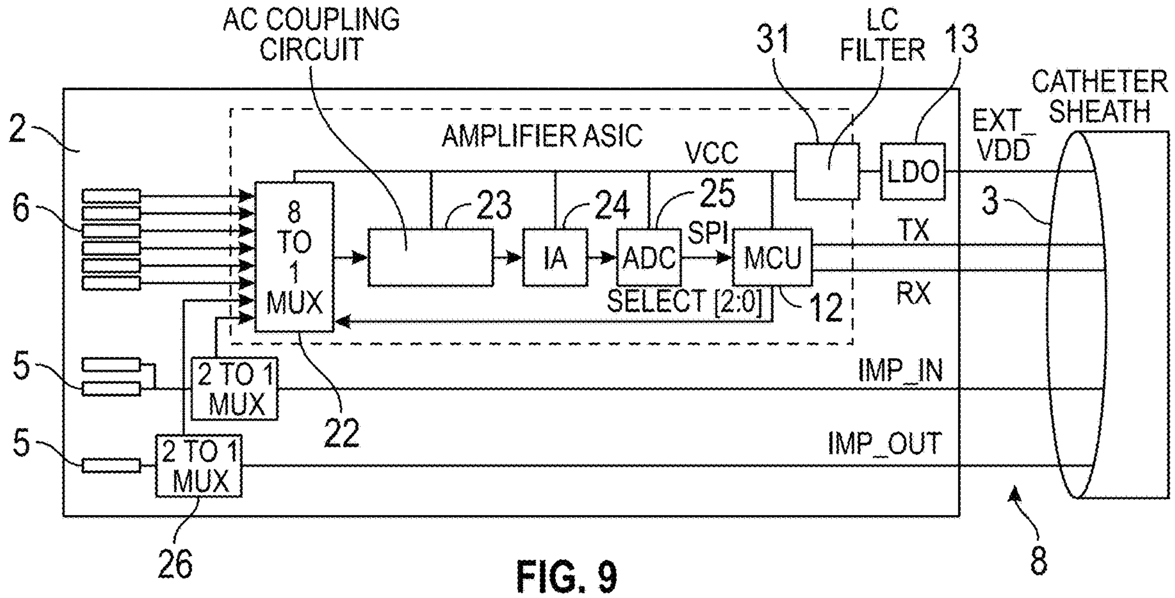
FIG. 9 is a circuit block diagram of the Huygens catheter circuitry showing the amplifiers deployed on the catheter electrodes and the impedance sensing electrodes from a figure in the Incorporated application A CATHETER FOR CARDIAC AND RENAL NERVE SENSING AND MEDIATION, U.S. patent application Ser. No. 17/468,460.
Figure 10:
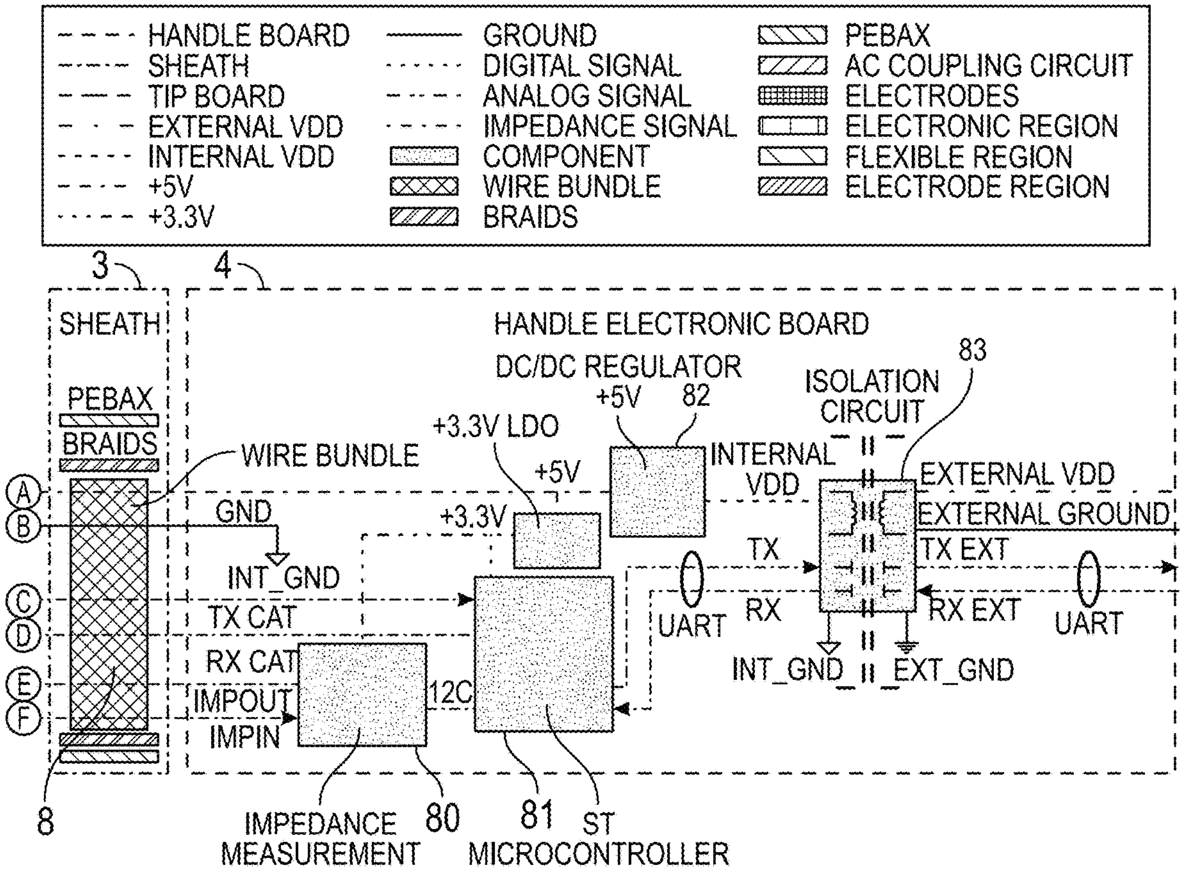
FIG. 10 is a circuit block diagram of the impedance measurement circuitry used in the Huygens catheter from a figure in the Incorporated application A CATHETER FOR CARDIAC AND RENAL NERVE SENSING AND MEDIATION, U.S. patent application Ser. No. 17/468,460.

The application of local pre-amplification to measure bioelectrical potential, with sufficient SNR reduction as well as bandwidth, transforms the art of measurement in electrophysiological studies from the current state of phenomenological correlations to a bottom-up discipline, where observations are anchored in a common mode application of the biological substrate and the measuring apparatus, and where matrices of such measurements are defined by what we term as a "standard model" employing addressable and measurable "elementary building blocks." The "standard model" is the prior art method of defining "phase singularities" in a post-processing method using an analog signal with large noise content. The disclosed embodiment eliminates noise content by measuring the DC potential locally, and which is thereafter locally amplified and digitized into a word that cannot be corrupted by noise-generating sources. The Huygens sensing array has a resolution of 5-25 μV which the prior art standard model cannot resolve. The disclosed methodology simultaneously measures the impedance of tissue contact therefore providing two fundamental data points which are not interpolated mathematically, but are obtained through a direct measurement from the tissue in real time. The disclosed methodology incorporates an "elementary" data set for the measured vector which is the order tuple of position P, orientation O, impedance Z, DC voltage potential, time t: <P(xyz), O(xyz), Z, V, t>. FIG. 9 is a circuit block diagram of the Huygens catheter circuitry showing the amplifiers deployed on the catheter electrodes and the impedance sensing electrodes from a FIG. 4B in the Incorporated application A CATHETER FOR CARDIAC AND RENAL NERVE SENSING AND MEDIATION, U.S. patent application Ser. No. 17/468,460. FIG. 10 is a circuit block diagram of the impedance measurement circuitry used in the Huygens catheter from a FIG. 5 in the Incorporated application A CATHETER FOR CARDIAC AND RENAL NERVE SENSING AND MEDIATION, U.S. patent application Ser. No. 17/468,460. The operation and details of the elements shown in FIGS. 10 and 11 are further described in the incorporated application and illustrate the referenced local amplification and simultaneous impedance measurement discussed in this disclosure.

Many studies have demonstrated that fibrillatory rhythms are not random phenomena, but rather have definable patterns (Kadish A, et al., "Characterization of fibrillatory rhythms by ensemble vector directional analysis." Am J Physiol Heart Circ Physiol. 2003 October; 285(4):H1705-19. Epub 2003 Jun. 5). However, prior art mapping techniques have limitations in their ability to identify the organization of fibrillation. The purpose of the illustrated embodiments of the invention is to develop and apply a method for detecting the energetic event by the ability of local amplifier with its inherent variable resistor Huygens™ sensor module to generate, for example, an "ensemble vector mapping" to characterize the spatiotemporal organization of fibrillation.

Catheter-based ablation has revolutionized arrhythmia management by offering the most definitive treatment for virtually all types of tachyarrhythmias. The reasons behind the success of ablation are many, but chief among them is the ability of the electrophysiologists to identify underlying mechanisms and to precisely localize and eliminate the tachycardia foci or circuits. Unfortunately, mapping of high-dominant-frequency areas has been shown not to be effective in chronic atrial fibrillation (AF) patients. On the other hand, mapping of complex fractionated atrial electrograms (CFAE) as target sites for AF ablation has shown great promise. During sustained AF, CFAEs often are recorded in specific areas of the atria and exhibit surprisingly remarkable temporal and spatial stability. CFAEs usually are low-voltage electrogram (0.05 to 0.25 mV) with highly fractionated potential or with a very short cycle length (≤120 ms). See Koonlawee Nademanee, "Trials and Travails of Electrogram-Guided Ablation of Chronic AtrialFibrillation", Circulation. 2007; 115: 2592-2594

This is an important observation that a complex arrhythmia cannot be assumed to be defined as well as treated unless the underlying mechanism and precise identification of the vectorial direction as well as its magnitude can be established. The notion that the native signal-measurement can somehow can be improved through a smart algorithm or a sophisticated mathematical filtering, manipulated by recursive methods, and/or wavelet analysis, is a misleading one. The native signal cannot be improved beyond its energy domain in its time scale or its geometric spacing. The signal noise components (SNR) and their representations cannot be altered by a post-processing approach. In contrast we teach a technological departure from the electrode technology with its post-processing approach, which is the mainstay of the prior art of biopotential data acquisition.

The operative departure is the incorporation of local amplification at the source using, for example, a Huygens™ sensor module in an array form with geometry configurations such as bipolar, quadripolar, decapolar, or any array with 64 or more electrodes, to enable a multitude of electrodes/pads to simultaneously capture the complex electropotential energetic event, with the improved SNR and sampling rate commensurable with the bandwidth and accuracy on the spatio-temporal domain. A mature scientific theory is characterized by its power of prediction to uniquely project an outcome based on boundary conditions that can be reproduced, where the specificity of the well-formed question results in a well-defined answer. The art of EP is in need of a radical review of its methodologies with regard to the relationship between its diagnostic findings and its loosely correlated clinical observations.

As an example of the prior art clinical literature describing the underlying mechanism of patients with supraventricular tachycardia and paroxysmal atrial fibrillation consider the following statement. "Each patient underwent a baseline electrophysiologic study with closely spaced electrode catheter. . . . Paroxysmal atrial fibrillation (PAF) frequently occurred in patients with paroxysmal supraventricular Tachycardia (PSVT). However, the mechanisms responsible for the occurrence of PAF were not fully understood. Although previous studies have suggested that atrioventricular (AV) accessory pathway or slow AV node pathway itself may play an important role in the genesis of PAF, disturbed atrial electrophysiology during PSVT may be the other mechanism of initiation of PAF. Klein et al. have shown increased atrial refractoriness during PSVT and considered mechano-electrical feedback a cause of PAF during." Chen Y, et al. "Role of atrial electrophysiology and autonomic nervous system in patients with supraventricular tachycardia and paroxysmal atrial fibrillation", J Am Coll Cardiol. 1998; 32(3):732-738

It is clear from this statement that while the underlying cause is nested within multiple potential explanations relating to the mechanism that might lead to such conditions, no unique underlying mechanism was cited. The literature as noted above provides the explanations that the variability of the identifications provided by studies, yields different mechanisms for the causes and its underlying mechanism, as discussed by the in many of the clinical studies are fashioned along the general outline shown above by Li et al.

The complexity is clarified in why such conditions manifest themselves in the specific class of PAF: a conventional model for any assessment of the boundary conditions must be first subject to the ability of the measurement and its methodology including its measuring apparatus to yield consistent and repeatable data under similar conditions. The ambiguity and non-unique distinction of the mechanism generating the condition is a typical narrative in many clinical discussions and intellectual chatter of the various conferences on the topic of the underlying mechanisms of arrhythmogenic causes. In order to improve the art of measuring apparatus we employ a platform comprising a local amplifier using Huygens™ sensor array located at the target site to enable the mining of bioelectrical potential with fidelity and repeatability not currently available in the discipline of EP studies.

The aim to form a standard model for EP is centered on the fact that the etiological as well as morphological elements forming the substrate of a biostructure must obey unique boundary conditions so that their specificity can be studied and reconstructed as well as predicted. The fact that most of the EP studies are a collection of phenomenological observations supports the contention that EP as a scientific discipline must undergo a change which must first be organized under the tool set and the ability of the physicians' community to recognize a generally accepted standard of data capture as well as a data format. The fact that many researchers and their publications tend to exhibit colorful plates with interesting isochrones does not constitute a "standard model," as the collection methods vary and its solution has a low predictability and reproducibility value.

Huygens™ technology improves the art of EP by creating such a standardized model, unifying the diagnostic observations under a measurement technique able to define the electrocardiogram (EGM) as energetic events, distinguishing such applications from the massive digital signal processing (DSP) manipulation customary in the prior art.

An overall view of the field of EP reveals a landscape of phenomenological collections of data with little to no specificity associated with the fact that the cellular excitable matrix is the result of specific etiological characteristics of the underlying substrate. If these data points were anchored by a robust physical and biological model, it will enable a simple translation between the electrical map and its substrate. Hence, the substrate will be directly correlated to the pathophysiology.

This state of affairs is dependent on the ability of the roaming catheter to collect the electrical potential and place such data on its anatomical target synchronously. Additionally, the signal must be distinguished from its noise components to separate the native signal effect of the far-field component and its near-field contributing element.

The fundamental technique of local amplification provides the user with native local signal where the near-field as well as its far-field component can be distinguished without post-processing employing algorithmic "gimmicks" and other sophisticated DSP manipulations.

The disclosure is directed to a technology for capturing bioelectric potential data, which is anchored in measurement techniques that reveal the physical nature of a biological substrate's electrical properties. This technology allows for the interpretation of the phenomenological expression of the electrogram (EGM) and its graphical representation in the context of an energetic event, based on the dielectric ($\kappa$) and conductivity ($\sigma$) measurements of underlying tissues.

Electrophysiology studies employ a variety of devices, specifically catheters with different electrical configurations of electrodes using magnetic as well as electrical impedance techniques to form an electro-anatomical map. The fact that electroanatomic mapping fails to connect the inherent physical relationship between an energy transfer function and its causal dependency on the substrate, as represented by the electrogram, is the foundation for the utility of the local amplification, exhibited herein via the use of a Huygens™ sensor array shown in FIG. 11 for conducting electrophysiological studies.

Figure 5:
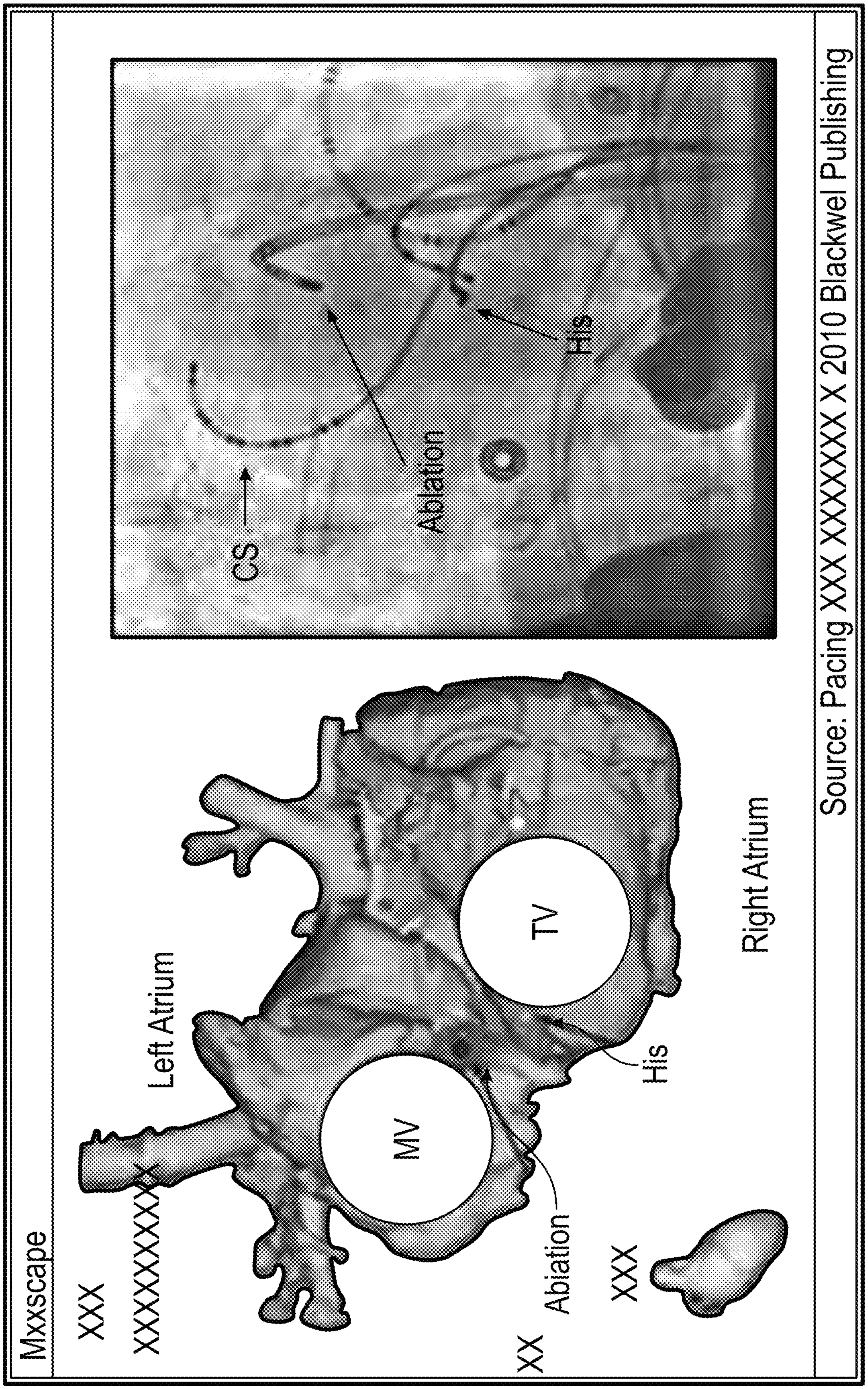

The method and exemplary apparatus which is presented enables the creation of an electroanatomic map in FIG. 5 with high fidelity and accuracy while depicting a local electrogram with its native dynamics, its geometrical as well as its time domain specificity and further providing for reconstruction of the anatomical and the extrapolated etiological characteristics of the cellular matrix by employing the Huygens™ sensor array apparatus.

Figure 4:
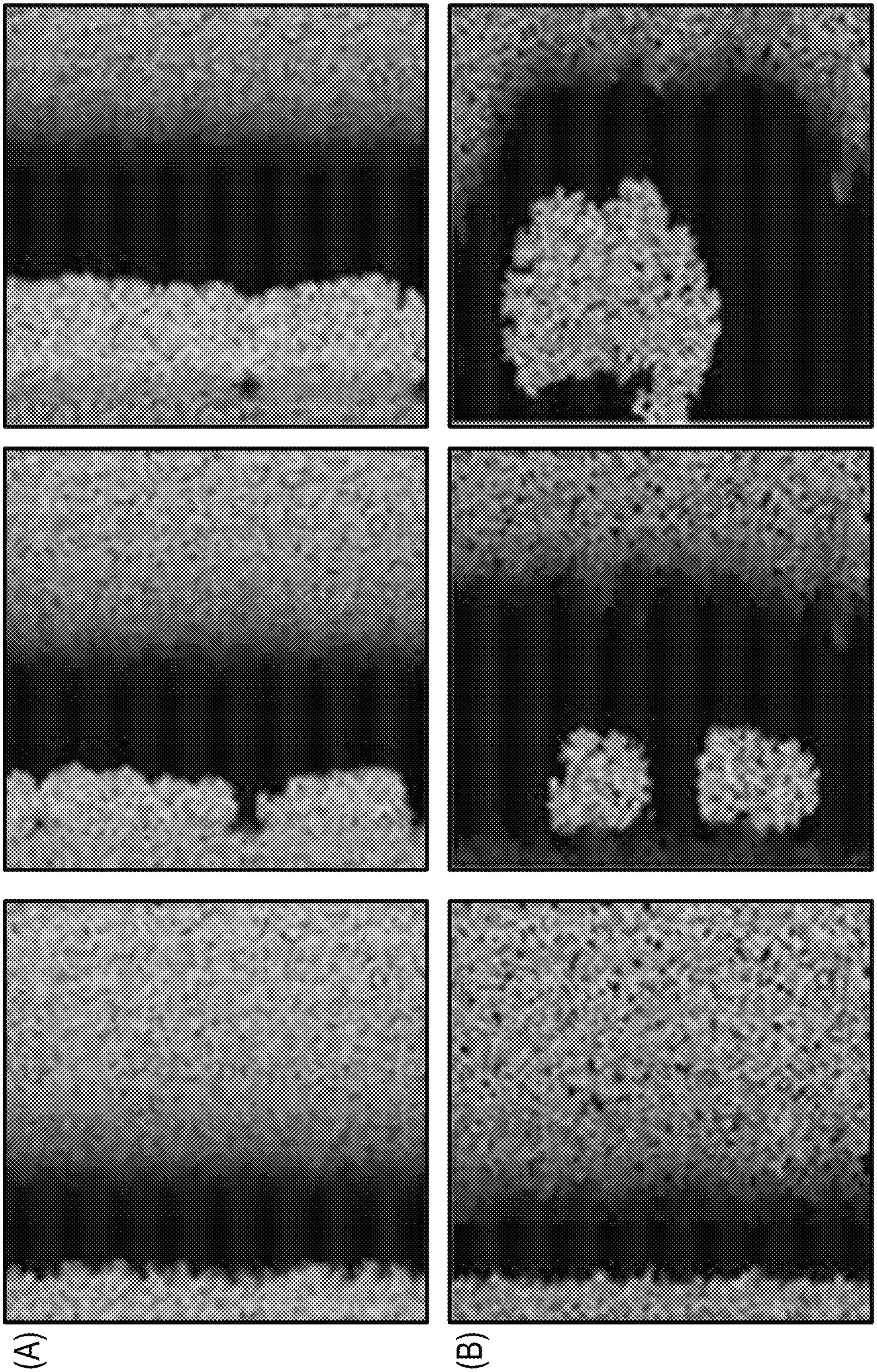
FIG. 4 illustrates the vulnerability to wave break and spiral wave formation due to diffuse fibrosis.

The aim and utility of this local amplifier technology is to connect the phenomenological data with clinical observations. The electrical properties of the conduction path within the substrate and its etiological constituents (e.g., cellular matrix composition and its electrical counterparts) are correlated without the need to create a causal dependency after the fact. This allows for the formation of a robust and coherent standard model in forming the diagnostic basis for defining a disease model, as noted by Tusscher et al.'s study presented at Europace. The study notes, "During aging, after infarction, in cardiomyopathies and other cardiac diseases, the percentage of fibrotic (connective) tissue may increase from 6% up to 10-35%. The presence of increased amounts of connective tissue is strongly correlated with the occurrence of arrhythmias and sudden cardiac death." Tusscher, Panfilov. "Influence of diffuse fibrosis on wave propagation in human ventricular tissue." Europace (2007) 9(suppl 6): vi38-vi45 doi:10.1093/europace/eum206. FIG. 4 illustrates the vulnerability to wave break and spiral wave formation due to diffuse fibrosis. FIG. 4 shows three snapshots in upper row A of the progression of two wavefronts initiated in a medium with 10% fibrosis and with a coupling interval of 321 ms between them; and three snapshots in lower row B of the progression of two wavefronts initiated in a medium with 30% fibrosis and with a coupling interval of 320 ms between them.

Because of its high success and low morbidity rates, radiofrequency (RF) catheter ablation has become first line of treatment for many arrhythmias. In this procedure, one or more electrode catheters are advanced percutaneously through the vasculature to contact cardiac tissues. A diagnostic study is performed to define the arrhythmia mechanism, and subsequently an ablation catheter is positioned adjacent to the arrhythmogenic substrate. Radiofrequency energy of up to 50 W is delivered in the form of a continuous unmodulated sinusoidal waveform, typically for 60 seconds. The arrhythmia is eliminated via the destruction of arrhythmogenic tissues (e.g., accessory pathways) and its subsequent replacement with scars.

Figure 7:
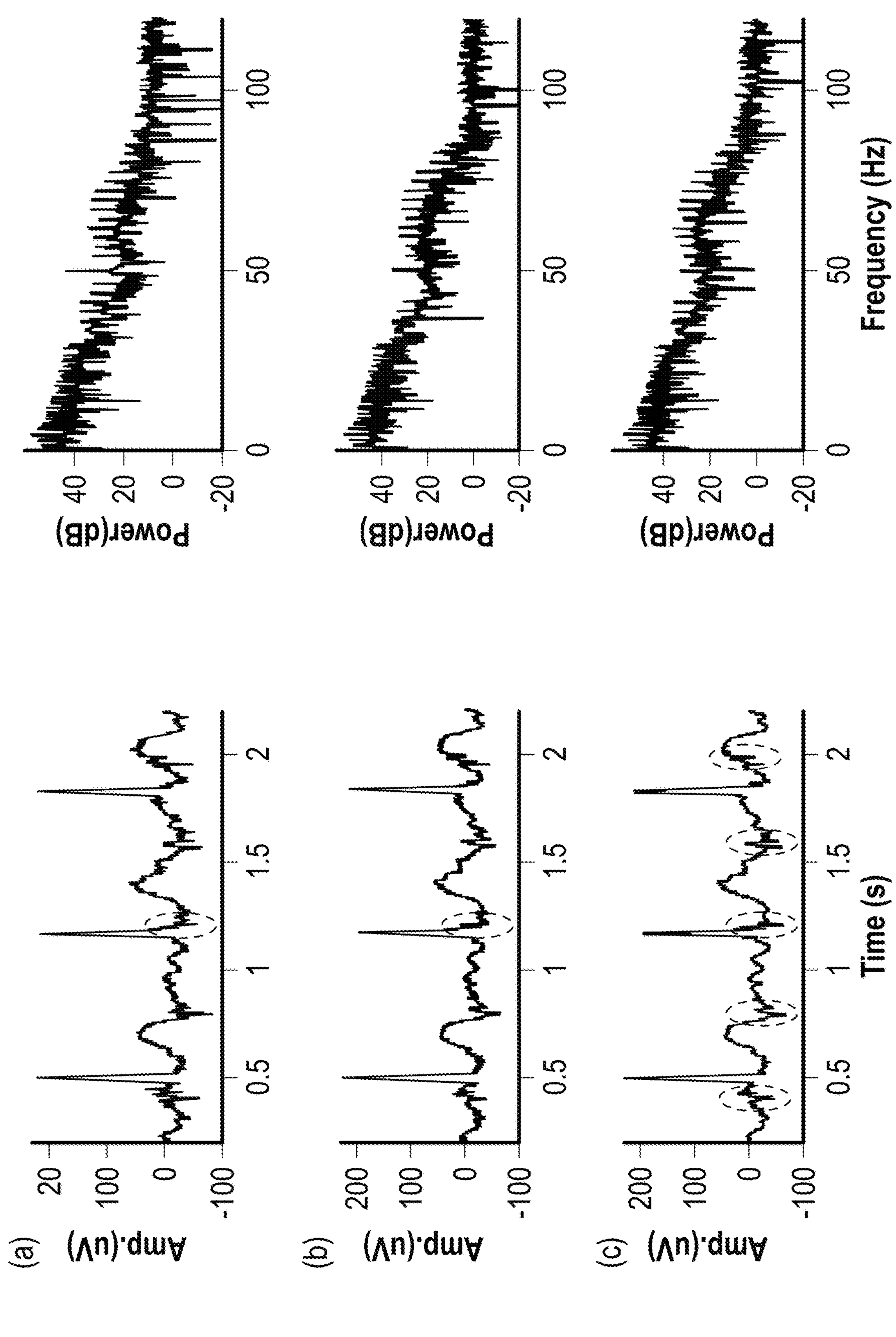
FIG. 7 are three traces of the cardiac amplitude and corresponding power spectrographs of the cardiac signal.

FIG. 7 illustrates the vulnerability to wave break and spiral wave formation due to diffuse fibrosis. FIG. 7 shows three snapshots in upper row A of the progression of two wavefronts initiated in a medium with 10% fibrosis and with a coupling interval of 321 ms between them; and three snapshots in lower row B of the progression of two wavefronts initiated in a medium with 30% fibrosis and with a coupling interval of 320 ms between them.

In the electrogram approach in FIG. 5, because precise lesion placement is required, arrhythmias for which ablation are most effective (e.g., accessory pathways, atrioventricular nodal re-entry tachycardia [AVNRT]) have largely anatomically based or directed substrates. An electrode catheter in the coronary sinus outlines the mitral annulus fluoroscopically, and is used to guide ablation catheter position. The relative amplitude of the atrial and ventricular components of the bipolar electrogram recorded by the ablation catheter further defines the tip position relative to the annulus. The earliest atrial or ventricular activation during pathway conduction identifies pathway location along the annulus. The target for catheter ablation of AVNRT occurs even more predictably in the posteroseptum. Ablation may be guided entirely by anatomic location relative to the HIS bundle and coronary sinus catheter positions, which serve as fluoroscopic landmarks, or by a combined anatomical and electrophysiological mapping, such as those generated by CARTO™ or EnSite®.

Complex Arrhythmias and the Limitations of Prior Art

Figure 6:
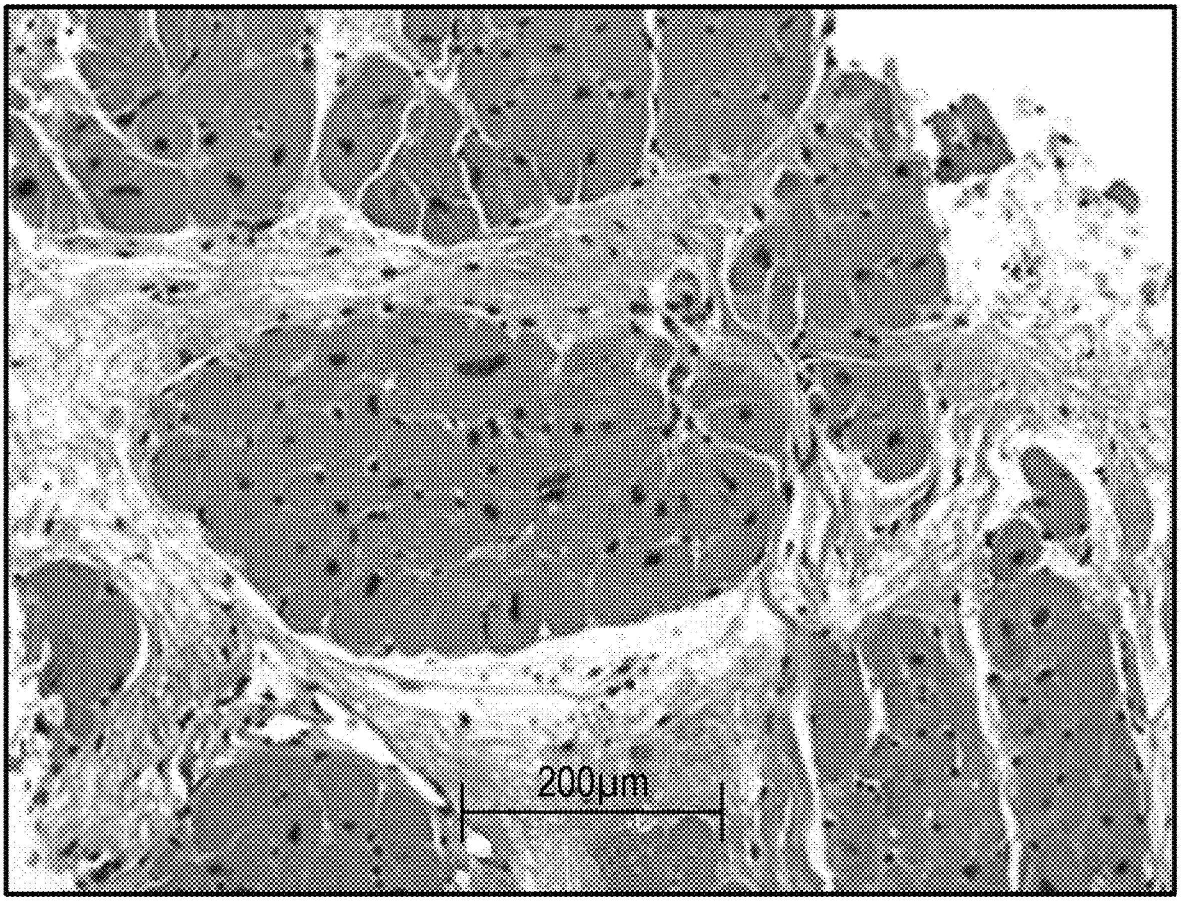
FIG. 6 is a fluoroscopic image used with a prior art mapping catheter and sensory apparatus, which cannot accurately locate both the geometry and time domain of the wavefront's activity generated by the "avalanche" of the cellular excitable matrix.

However, ablation of more complex arrhythmias, including some atrial tachycardia, many forms of intra-atrial re-entry, most ventricular tachycardia, and atrial fibrillation continue to pose a major challenge (PA Friedman, "Novel mapping techniques for cardiac electrophysiology", Heart. 2002 June; 87(6): 575-582). The current art of mapping lacks sufficient resolution to capture the complexity of the substrate fibrotic tissue and the collection rate lacks a sufficient sampling rate to address the dynamic range of the wave form dynamics. Both problems are addressed by the Huygens catheter with its SNR improvements, its dynamic range of 1 KHz. This challenge stems, in part, from the foregoing limitations of the conventional fluoroscopy used in FIG. 6 as well as in the construction of prior art mapping catheters and sensory apparatus, which cannot accurately locate both the geometry and time domain of the wavefront's activity generated by the "avalanche" of the cellular excitable matrix. Thus, the primary disadvantage of the existing and prior art of electrode technology is in its inability to account for the cellular biopotential transfer with the resolution necessary to capture the energetic event, and the insufficiency of the prior art electrode technology to account for ionic transfer time depicting the actual energetic event, measuring and representing the "avalanche" dynamics of this bioenergetic event.

The aim of using transistorized electrodes (i.e., the Huygens™ local amplifier circuit) is to accurately identify the conduction path in the heart tissue. An ideal conductor might, in general, satisfy the accuracy representation employed by the prior art, but in disease modeling, most of our assumptions relating to linear behavior of the conduction path (the cable theory) cannot be reproduced by such modeling, due to the impact of secondary and significant noise generating phenomena, such as vectorial multiplicity of sources generating the EGM, magneto-electric anisotropy, and conduction in the cardiac strand where gap-junction-mediated mechanisms alternate. Conventional 'cable theory' does not satisfy the ionic conservation law, and the Navier-Stokes equations with its diffusion modeling might be a better approximation of the ionic heart conduction, and its energy vector with its magnitude and direction than is provided by the cable theory.

An obvious problem in separating the noise component from the native signal is the inability of the system to identify which is noise and which is the native signal in FIG. 7. If we know that a signal is smooth or changing slowly and that the noise is fluctuating rapidly, we can filter out noise by averaging adjacent data to eliminate fluctuations while preserving the trend. Noise can also be reduced by filtering out high frequencies. For smooth signals, which change relatively slowly and therefore are mostly lower frequency, this will not blur the signal too much. Many interesting signals are not smooth; they contain high-frequency peaks. Eliminating all high frequencies mutilates the message, namely "cutting the daisies along with the weeds," in the words of Victor Wickerhauser of Washington University in St. Louis, adequately expresses the main drawback of post-processing such signal wavefronts (B Hubbard, "The World According to Wavelets: The Story of a Mathematical Technique in the Making", Natick, MA: A K Peters, 1998).

Signal-to-Noise Ratios

High signal-to-noise ratios (SNR) thus requires the use of a very low-noise amplifier with a limited bandwidth. The current technologies provide a differential amplifier with voltage noise of less than 10 nV √1 Hz and current noise less than 1 pA. However, both parameters are frequency-dependent and decrease approximately with the square root of frequency; the exact relationship depends on the technology of the amplifier input stage. Field-effect transistor (FET) preamplifiers exhibit about 5 times the voltage noise density compared to bipolar transistors and a current noise density that is about 100 times smaller.

In summary, the problem of reconstruction of the electrophysiological activity in the prior art is two-fold: first, in the architectural design of the use of electrodes and their associated electrical circuit design, and secondly, in the further handicap caused by modeling the biopotential activity as a physical phenomenon, whereby excitable cells are modeled by employing the cable theory with isotropic behavior. The use of electrodes and cable theory is a good approximation of idealized conditions of such energetic events, but suffers from the inability to associate accurately the intracardiac electrogram with a specific endocardial site which also limits the reliability with which the roving catheter tip can be placed at a site that was previously mapped. This results in limitations when the creation of long linear lesions is required to modify the substrate, and when multiple isthmuses or "channels" are present. Additionally, since in conventional endocardial mapping a single localization is made over several cardiac cycles, the influence of beat-to-beat variability on overall cardiac activation cannot be known.

The sensory apparatus and methods we teach captures the complexity, as well the time domain, of such energetic events synchronously. The Huygens™ sensor array and its fidelity further mimics the underlying dynamics, and improves conventional catheter-based mapping techniques by localizing and identifying precisely the arrhythmogenic substrates that are removed from fluoroscopic landmarks and lack characteristic electrogram patterns.

Modelling of Bioelectrical Activity and Diffusion

The need to improve modeling of cellular electrical activity is central to physiology and electrophysiological studies. Biopotential recording and mapping of such electrical activity enables the physician or researcher to form and fashion his or her understanding of the fundamental data gathering and analysis of such diverse biological activities as sensory perception, communication between neurons, initiation and coordination of skeletal-muscle contraction, synchronization of the heartbeat, and the secretion of hormones. Most mathematical models of cellular electrical activity are based on the cable model, which can be derived from a current continuity relation on a one-dimensional ohmic cable. As such, its derivation rests on several assumptions: ionic concentrations are assumed not to change appreciably over the time of interest, and a one-dimensional picture of cell geometry is assumed to be adequate for purposes of describing cellular electrical activity. These assumptions, however, may not hold in many systems of biological significance, especially in the central nervous system and within cardiac tissue, where micro-histological features may play an essential role in shaping physiological responses.

The first and far most assumption of electrophysiological mapping is the notion of linearity as well as homogeneous conduction path, both are refuted in light of the clinical observation associated with ephaptic coupling effect on the conduction path well as magnetic heart vector anisotropy, both affect the ECG representation and its informative content. The corruptive measure of the electrogram fidelity and its true nature as to the native signal is highlighted herein.

Signal Anisotropy—Ephaptic Coupling

There are many contributions to the resultant signal shown by the electrogram, we mention two of the organizing principles which if accounted for under the conventional method of capturing the electrogram clearly demonstrate the shortcomings of the prior art. The first principle of organizing the electrogram set is the 'cable theory' and the second principle of organizing the biopotential activity is the ability of the representation system to account for the complementary 'magnetic vector' impact on the ionic cellular matrix. In both of these principles and their accompanying observations, no filtering methods of any sort improve the native fidelity of the signal. It is further shown by observations and analytical methods that any attempts to reconstruct such activity artificially by post-programming activity are doomed to fail, as these inherent bioelectrical activities (ephaptic, electromagnetic) are fundamental elements of the native signal. Ephaptic coupling is a form of communication within the nervous system and is distinct from direct communication systems like electrical synapses and chemical synapses. It may refer to the coupling of adjacent (touching) nerve fibers caused by the exchange of ions between the cells, or it may refer to coupling of nerve fibers as a result of local electric fields. Simply stated, the cable theory representation is an ideal depiction of the conditions generating the biopotential cellular avalanche, and it properly accounts for and describes the isotropic influences, but lacks the ability to discern influences such as magnetic heart vector and ephaptic coupling.

Ephaptic coupling can't be 'washed' out by some filtering; its effects must be accounted for by measuring its influence on the conduction path. This major drawback of the prior art, whereby the dynamics of the ionic potential with the necessary fidelity mimicking the actual energetic event are not accounted for. An example of such influence is the contribution of the cardiac gap junctions which play a pivotal role for the velocity of impulse propagation in cardiac tissue. Under physiologic conditions, the specific sub-cellular distribution of gap junctions together with the tight packaging of the rod-shaped cardiomyocytes underlies anisotropic conduction, which is continuous at the macroscopic scale. However, when breaking down the three-dimensional network of cells into linear single cell chains, gap junctions can be shown to limit axial current flow and to induce saltatory conduction at unchanged overall conduction velocities. In two- and three-dimensional tissue, these discontinuities disappear due to lateral averaging of the depolarizing current flow at the activation wavefront (S Rohr, "Role of gap junctions in the propagation of the cardiac action potential", Cardiovasc Res (2004) 62 (2): 309-322). In this theory, the cellular path is represented as a cable, and hence it is referred to as "cable theory" (Lin & Keener, "Modeling electrical activity of myocardial cells incorporating the effects of ephaptic coupling", PNAS. Dec. 7, 2010; 107(49): 20935-20940), or the mathematical modeling of bioelectrical current along passive neuronal fibers. Existing hardware employing electrode technology, coupled with the general algorithmic representation of the biopotential dynamics under such theory (both hardware and cable theory) suffer from the above-mentioned limitations, which are eliminated by the use of a local amplifier, such as a Huygens™ sensor array, and its method of map reconstruction.

As outlined above the effect of ephaptic coupling as an inherent source of anisotropic behavior, impacts the conduction path of the bioelectric signal and its influence, and is well expressed in cases such as described in FIG. 11 (Mori Y, et al., "Ephaptic conduction in a cardiac strand model with 3D Electrodiffusion", Proc Natl Acad Sci USA. 2008 Apr. 29; 105(17):6463-8). This and other examples in vitro, as well as in vivo animal studies, demonstrate that conduction velocity and gap junction parametrics play a significant role in the formation of the conduction path and its origin, and can be shown as the result of the etiology of the cellular matrix change due to fibrotic formation. The ephaptic coupling is only one argument out of many cited above in support of our advocacy of using the Huygens™ sensor array in acquiring the biopotential signal. The use of impedance spectroscopy in the form of a Huygens™ sensor array provides for accurate representation of the bioelectric signal; due to its inherent electrical characteristics.

Signal Anisotropy, Modeling Bipotential Activity with the Poynting Energy Vector (PEV)

Figure 8:
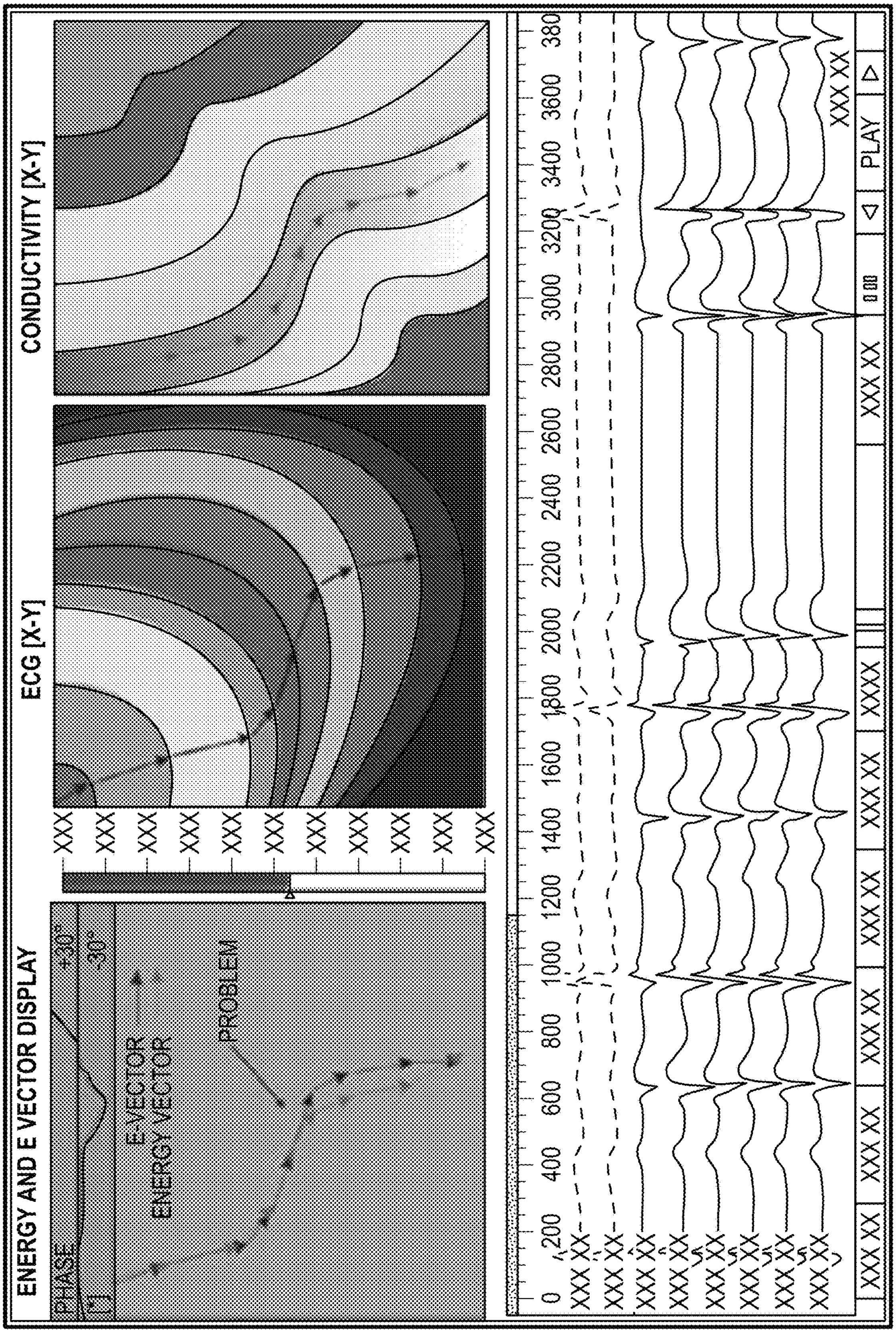
FIG. 8 is a set of color graphs of an energy and E vector display, ECG and conductivity map over a time graph of an EP signal showing how the location of a rotor or other endocardial blockage is determined.

According to the present disclosure the analytical relationship between conduction path and the vectorial representation of anisotropic influence of the magnetic dipole vector on the conduction path provides a better determination of cardiac function. The behavior of the Poynting energy vector (PEV) shows that a representation of the ECG signal with its post-processing modality is a very crude approximation of the native bioelectric signal. The argument relating to the ephaptic coupling influence on the conduction velocity is supplemented by the magnetic heart vector's (MHV) contribution to the conduction path geometry and its timing, including synchronicity. Analytical evidence for anisotropy is noted when we employ Maxwell's equation. The data analysis and extraction of additional diagnostic (and as a corollary, the pathological diagnostic) information of the substrate is revealed when we create a map as shown in FIG. 8, where we superimpose the electric and energy waves as shown in a SPICE simulation (Simulation Program with Integrated Circuit Emphasis) converging the electric with the magnetic heart vector influence by computing impedance (Z) value generated from the substrate. The rightmost panel in FIG. 8 is a map of the heart conductivity paths. A central green arrow path maps out the path of a heathy patient having no anisotropies in the heart conduction pathway. The ECG map shown in the center panel of FIG. 8 is a map of the electrical heart wave in the cardiac field as marked by the pathway of black arrows. These two traces are superimposed on each other in the leftmost panel in FIG. 8 where it can be seen that the energy or PEV wave marked by the orange arrows diverges at a point from the electrical wave given by the ECG map. The point of divergence of the two pathways indicates an anisotropy in between the direction of energy flow of the heart wave and the electric wavefront flow of the heart wave. This is indicative of the phase shift from orthogonally between the electrical and magnetic wave components in the heart wave. The anisotropy may be a site of scar tissue or a rotor, which is the cause of AF and if ablated may result in eradication of AF. Ablation then only at the points of divergence indicated in the superimposition diagram of FIG. 8 results in a electrophysiological directed or optimal ablation procedure characterized by reduced procedure time and increase efficacy.

The measure of impedance is derived from an injection of a small current via the AC circuit to obtain a measure of conductivity of the tissue. Measuring the potential in microvolt-millivolt range we can estimate the anisotropic verses the isotropic wave conduction path. Since the conductivity of the medium is a representation of the conduction path, and if no fibrotic tissue-insulator or scar tissue is on the conduction path, the wave form travel path will follow a zero-phase shift (beta-90 degree will equal=0). But the conduction path in FIG. 8 did not follow the conductivity measure, hence there will be a phase shift of Beta−90 degrees>0.

The measure of impedance is a form of injecting a small current via an AC circuit to obtain a measure of conductivity of the measured tissue. Measuring the potential in microvolt-millivolt range, we can estimate the anisotropic verses the isotropic wave conduction path. Since the conductivity of the tissue medium is a representation of the conduction path, and if no fibrotic tissue-insulator or scar tissue is in the conduction path, the waveform travel path will follow a zero-phase shift (beta−90 degree will equal=0). But if the conduction path does not follow the measured conductivity, there will be a phase shift of beta−90 degrees greater than 0.

To overcome the measurement limitations and supplement the clear clinical findings of myocardial anisotropy, we observed that simultaneous localization and mapping (SLAM) magnetic fields during the cellular activation sequence uncovers the magnetic heart vector (MHV) by computing a vector derived from Maxwell's equations, a process of data collection available only if we derive the PEV from the impedance vector (Z) using the Huygens™ sensor array supplemented with a computational algorithm. Clinical observations reported (J. Malmivuo, et al. "Bioelectromagnetism", Oxford University Press 1995) that measuring the angle between vectors of an equivalent electric dipole (electric heart vector, EHV) and magnetic heart vector or dipole (MHV) provides significant corollary information about the myocardium conductivity. The overall anisotropic case of the myocardium conductivity is represented by a tensor (Gerardo I et al., "Knowledge-based tensor anisotropic diffusion of cardiac magnetic resonance images", Medical Image Analysis (1999) volume 3, number 2, pp 1-25: Oxford University Press). The degree of anisotropic conductivity manifestation is characterized by the angle along the transverse and axial conductivity paths.

The solution for measuring and deriving the relationship between the EHV and its respective MHV, which supplements the analytical mapping with information about the myocardium conductivity and anisotropy, is derived from Maxwell's equation as the PEV. The PEV is constructed from the potential and impedance vectors of the measurements. In one application of the Huygens™ sensor array, a mapping catheter is used for biopotential sensing. The phase difference $\beta$ between the PEV and EHV is measured and is used to infer the features of anisotropy in the myocardium. The anisotropy of conductivity is uniform; that is to say, the change of activation energy generated and consumed by the ionic diffusion process is within the activation region of the measurement. The assumption is a healthy heart where there is no anisotropy in conduction path because the dielectric media formed by the excitable cells is uniform. Once scar tissue or fibrotic tissue is in the path, the permeability ($\mu$) is changed, and the wave is shifted due to changed dielectric value. Hence there is a capacitive load which delays and/or prevents electrical charge transfer. Anisotropic shift is represented by the angle data of 90 deg−$\beta$.

Thus, the volumes of integration are accurate with a margin of error reduction based on independent statistical samplings of the measured site over multiple heartbeats. "Accurate" means that the statistical measure is the averaging of the waveform relative to the QRS clock registered by the electrogram.

The PEV derivation is based on the law of energy conservation when used for the time period over two QRS cycles to acquire the initial baseline data foundation to form the map. The validity of the PEV derivation is corroborated by the fact that the activation spread obeys a mathematical identity, namely the phase angle relationship between B (magnetic) and E (electrical) fields are at 90 degrees perpendicularity as defined by the formalism of Maxwell's equations. The PEV directly exhibits the E and B fields' phase angle relationship. The integral form of Maxwell's equations leads to the PEV, and to the substitution of E and Z derivations of PEV. The following set of derivations from Maxwell's time dependent equations provides a formal basis for the clinical observations of a Huygens™ sensor array to derive the Z impedance vector, hence demonstrating that the conduction path is measurable. The inverse method, namely substituting the B (magnetic flux density) and the Z (impedance value) formally in the $2^{nd}$ varying Maxwell equation, and with the resultant PEV (Poynting Energy Vector) further supports the argument that the nature of the resultant electrogram supplemented by the use of the Huygens™ sensor array enables a clinical derivation of PEV from Maxwell's equations. The availability of Z impedance vector is further evidence that the complex fractionated wavefront cannot be resolved by post-processing methodology as currently practiced by the use of conventional electrode technology.

The argument is shown below using Maxwell's equations.

By multiplying B and E respectively and subtracting Equation (2) from (1) and using vector identities yields (3) and (4).

$$\nabla \times E = -dB/dt \quad (1)$$

$$\nabla \times B = \varsigma\mu dE/dt + \mu J \quad (2)$$

$$B \cdot (\nabla \times E) = -B \cdot dB/dt \quad (3)$$

$$E \cdot (\nabla \times B) = \varsigma\mu(E \cdot dE/dt) + \mu(E \cdot J) \quad (4)$$

where $\varsigma$ is conductivity derived from the impedance measurement. Subtracting, rearranging and using vector identities yields Eq. (5) which simplifies as Eq. (6)

$$\nabla \cdot (E \times B) = B \cdot (\nabla \times E) - E \cdot (\nabla \times B) \quad (5)$$

$$\nabla \cdot (E \times B) = -d/dx(1/2B \cdot B) - d/dx(\varsigma\mu E \cdot E) - \mu JE \quad (6)$$

Integrating both sides of Eq. (7) over the volume V and within the boundary Y gives (8), which is a representation of the energy equation in which the first term is the energy flux out of Y boundary of V.

$$\nabla \cdot [(1/\mu E \times B)] + d/dx[\varsigma/2\, E^\wedge 2 + 1/2\mu\, B^\wedge 2] + J \cdot E = 0 \quad (7)$$

$$\int_y \frac{1}{\mu}(E \times B) \cdot dS + \frac{d}{dx}\int_v \left(\frac{\varsigma}{2}E^2 + \frac{1}{2\mu}B^2\right)dx + \int_v (J \cdot E)\, d\tau = 0 \quad (8)$$

The second term in Eq. (8) is the rate of change of the sum of the electric and magnetic fields; the third term is the rate of work within V done by the fields on the ionic charges. This third term in Eq. (8) assumes the inclusion of the energy of the multiple sources of cellular ionic charge exchanges, thus (9) leads to the PEV, as shown in (11) where s below is the measurement of impedance value Z and a subsequent measurement of the position and orientation of the distal end of the Huygens catheter. Such measurement yields the input data point (in a mapping system such as EnSite NavX of St. Jude as described in electroanatomical mapping by L. Gepstein and S. J. Evans: PMID "Electroanatomical Mapping of the Heart: Basic Concepts and Implications for The Treatment of Cardiac Arrythmias" where the position, orientation is performed by trilateration and the impedance by injection of ~2 millivolts of current to the endocardial tissue. The value of DC potential, Impedance and position/orientation of the catheter distal end indicate whether the site of such measurement computed by equation (8), yields the value of displacement (measured by angular displacement) leading to the results as shown in equation (12).

$$E = 1/\mu(E \times B) + s \text{ where } \nabla \cdot s = 0 \quad (9)$$

$$(\nabla \cdot \sigma)\nabla \text{V\_m} = 0 \text{ and } E = -\nabla \cdot \text{V\_m} \quad (10)$$

$$E = 1/\mu((E \cdot E)1/Z) + c \quad (11)$$

The parameter of interest is the angle β between the electric field and energy field; Eq. (12).

$$90° - \alpha = \beta \quad (12)$$

The vector E is obtained from energy vector field measurements by calculating the Z impedance vector; Eq. (11). By using the measured potentials $V_m$ and by employing Poisson equation, the E electric field is obtained, Eq. (10). Then, the PEV can be written as Eq. (11). The E vector and impedance Z can be calculated from the measured data points. The value obtained by the use of this mathematical procedure, 90°−α=β, indicates the maximal displacement between the magnetic heart vector (MHV) and the electric field. Such data is used to compute MHV—(which otherwise couldn't be measured directly), but by the use of the Poynting Energy Vector (PEV) technique, it is derived, thereby enabling the computation of the displacement of the MEV from its E electric field—using equation 10, the Poisson equation).

It should be noted that such derivation is possible only by the use of the impedance value Z measured by the Huygens sensor array, and its preferred embodiment where position and orientation of the catheter distal end is captured in a tuple including time, DC potential, impedance, and the vector position/orientation of the catheter, thereby performing the mathematical operation noted above by identifying the maximal displacement of the MHV and its location, thereafter enabling a therapeutic procedure to correct the possible arrhythmogenic cause for a pacing disturbance.

This is where the use of the Huygens™ sensor array plays the role of uncovering the substrate using the calculated impedance value Z which is used to plot the conduction path generated by the secondary effects associated with ephaptic coupling and the magnetic heart vector (MHV), both of which are inherent characteristics of the underlying substrate and cannot be manipulated by employment of post-processing filtering techniques. One can further calculate the angle β between the E field and E energy vector, where the difference is such that a display of the PEV energy vector is useful for cardiac disorder identification. The measurements of PEV energy data and Z conductivity data are collected from the electrocardiogramapping and ablation catheter for further processing and display of the resultant anisotropic data, enhancing the current method. The PEV indicates that there is a flux of energy where E and B are simultaneously present. The spread of the energy flux in the case of Maxwell's derivation is further defined by the wave equation (13).

$$\nabla \times E = -dB/dt \quad (13)$$

Taking the curl of each side, Eq. (14), yields Eq. (15), which is the wave equation (16).

$$\nabla \times \nabla \times E = -d/dx(\nabla \times B) \quad (14)$$

$$\nabla(\nabla \cdot E) - \nabla^\wedge 2E = -d/dx(\varsigma\mu dE/dt) \quad (15)$$

$$\nabla^\wedge 2E - \varsigma\mu(\partial^\wedge 2E)/(\partial t^\wedge 2) = 0 \quad (16)$$

Utilizing the above-described technique, the electrophysiological map can be accurately tailored using post-processing methodologies, such as diffusion tensor and geometric representation (e.g., Ricci flow geometry). (I Bakas, "The algebraic structure of geometric flows in two dimensions", 2005; V Ivancevic, "Ricci Flow and Nonlinear Reaction—Diffusion Systems in Biology", Chemistry and Physics. 2011.) The data generated by the Huygens™ sensory array, in contrast, can serve to enhance the existing formation of electrophysiological maps and provide substantial improvement in the art of biopotential measurement and analysis.

The resulting angular displacement of the MHV is then graphically indicated in the mapping created within the EnSite NavX and it is schematically illustrated by FIG. 8, where the measured Z impedance value is mapped using SPICE simulation against the electric potential and the magnetic heart vector. The resulting data collection shown in FIG. 8 is then graphically superimposed over the electro-anatomical map generated by the use of EnSite NavX® system (Endocardial Solutions, St. Jude Medical, Inc., St. Paul, MN, USA). The geometrical site(s) indicating the position of a divergence between the electric field (E) and the magnetic field (B) are then graphically displayed as focal points and indicated by the graphic as "energy and E vector display" and marked as "a problem" in FIG. 8. This schematic representation enables a diagnostic site for the operator to evaluate the treatment modality necessary such as it is customarily employed, namely a therapeutic application of ablation is employed to eliminate the focal sites of the pacing disturbance.

The use of the Huygens™ sensor array for mapping of electrophysiological attributes is centered on the formation of a junction by bipolar electrodes/pads between the cellular matrix and the contact surface of the bioelectrical signals generated by nerves and muscles, recorded as potentials, voltages, and electrical field strengths. The measurements involve voltages at very low levels, typically in the vast range from 1 μV-100 mV, with high source impedances and superimposed high level interference signals and noise. Furthermore, the signals are amplified for compatibility with devices such as displays, recorders, or A/D converters for computerized equipment. To adequately measure these signals, an amplifier must satisfy very specific requirements: (1) to provide selective amplification to the physiological signal, and (2) to reject superimposed noise and interference signals.

Local Amplifier Huygens Biopotential Measurements

The basic requirements that a biopotential amplifier such as the Huygens™ sensor array and its catheter structure must satisfy are: (1) The physiological process to be monitored should not be influenced in any way by the amplifier. No galvanic contact exists between the cellular surface and the conducting part of the sensor, thus preventing the occurrence of any Faradic current. (2) The measured signal should not be distorted. Ephaptic coupling as well as PEV must be accounted for by synchronously measuring such effects with suitable quality by the Huygens™ sensor array. (3) The amplifier should provide the best possible separation of signal and interferences. Near-field versus far-field phenomenon must be separated by mining the inherent differentiating elements without averaging such contributions. (4) The amplifier must offer protection to the patient from any hazard of electrical shock, such as using isolated FET and circuit architecture. (5) The amplifier itself has to be protected against damage that might result from high input voltages as they occur during the application of defibrillators or electrosurgical instrumentation and application of RF energy during ablation.

A fundamental aspect of clinical EP, the discipline of diagnosing and treating cardiac arrhythmias, is the interpretation of intracardiac electrical signal electrograms. All EGMs represent a voltage difference between two electrodes, whether the electrodes are in close proximity (e.g., bipolar EGMs) or at a relatively great or theoretically infinite distance (e.g., unipolar EGMs). A major disadvantage of unipolar recordings is that they contain a significant amount of "far-field" signal, i.e.: signals generated by depolarization of tissue remote from the recording electrode. The near-field signal exhibits a decay to zero potential along the X-axis, while the far-field indicates that the signal does not decay to zero potential, and is asymptotically parallel to the X-axis. Hence the use of the Huygens™ local amplifier with its variable resistor and ground at the site of measurement enables a clean separation between the far-field and near-field contribution to prevent the averaging of the resultant signal from the native measured potential. This advantage has an enormous contribution to the diagnostic value of the electrogram and can clearly improve the behavior of the ICD leads' optimal performance when detecting such a composite signal.

For example, EGMs from pulmonary vein ostia frequently manifest large far-field atrial signals recorded from regions that are at the border between the atrium and the pulmonary vein. Separating the signal of interest, in this case the pulmonary vein fiber potential (high-frequency signal) from the far-field atrial signal, which is a lower-frequency, and usually much larger signal, can sometimes be difficult, and requires pacing maneuvers and empirical RF energy application. In addition, differences in electrode sizes, for example a large ablation distal electrode compared to a smaller proximal electrode, might exaggerate the potential differences between the two electrodes and distort the resultant EGM signal amplitude, which is important for recording scar voltage. In addition, the direction of wavefront propagation influences the amplitude of the bipolar EGM, but not that of the unipolar EGM. Theoretically, a wavefront that propagates in a direction that is exactly perpendicular to the axis of the recording dipole would produce no potential difference, hence no EGM signal. The clinical significance of this scenario in mapping scarred tissue is unknown, as these maps are dependent on displaying areas of low voltage as areas of scarred myocardium.

Prior art intracardiac recording techniques, while they have served the clinician and basic scientists reasonably well over the past three to four decades, suffer from several inherent limitations, which this patent collection seeks to address, such as: (1) By the very nature of utilizing electrodes connected by long cables to a distant differential amplifier, these systems are subject to line "noise," ambient EMI, cable motion artifacts, and faulty connections. (2) Local signals are subject to recording of far-field signals, which at times render the interpretation of complex, rapid arrhythmias very difficult, if not impossible. (3) The conflation of far-field and signals of real interest, such as pulmonary vein fiber potentials, accessory pathway signals, and slow pathway potentials, can sometimes be the cause of failed ablations. The ability to record local electric activity with great precision and to the exclusion of far-field signals would be of paramount importance. (4) Current recording systems frequently cannot differentiate low-amplitude, high-frequency signals from background noise. Extremely low-amplitude signals, such as those generated during slow conduction within a myocardial scar, are frequently missed or lost in the background noise when amplifier gain is made sufficiently high to attempt to record such signals. (5) Continuous, low amplitude, fractionated high-frequency signals such as those frequently seen in the atria of patients with chronic atrial fibrillation, cannot be further characterized using existing recording technologies. These signals may contain important biologic and electrophysiologic information. For example, these signals may represent important areas of scarring that are responsible for formation of rotors. Alternatively, they may be manifesting discharges from contiguous epicardial parasympathetic ganglionated plexi.

In a near-field waveform the potential decreases monotonously with distance from the source, whereas an overlying far field source is constant and non-vanishing, representing the difference in potential between far-field and near-field (Cracco R Q, et al. "Somatosensory Evoked in Man: Far-field Potentials." Electroenceph Clin Neurophysiol 1976; 41:460-46). This difference between the waveform relative to the distance does not decrease over time, and can be subtracted by using a fast-acting local bipolar measurement available through the use of the Huygens™ sensor array.

In conclusion, the limitations in the prior art of electrode technology indicate the need to supplement the existing technology with a local amplifier technology, such as exhibited in the use of the Huygens™ sensor array. The Huygens sensor array may be geometrically configured as unipolar, bipolar, quadripolar, decapolar, and other linear arrays, and optionally as, for example, an 8×8 sensor matrix placed on a basket- or balloon-like structure, as well as incorporated into other related devices in various arrayed and matricular configurations.

These applications of the Huygens™ sensor technology offer great potential in the furthering of electrophysiological studies, including the understanding of the mechanisms of complex arrhythmias.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments include other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

What is claimed is:

1. A method for mapping subsurface scars comprising:

obtaining a catheter comprising a handle, a distal tip, a sheath that extends between the handle and the distal tip, a plurality of electrodes disposed on an external surface of the distal tip, the plurality of electrodes being configured to generate cardiac signal measurements, distal tip circuitry contained within the distal tip; handle circuitry contained within the handle and one or more communication elements formed within the sheath for interconnecting the distal tip circuitry and the handle circuitry, wherein a subset of the plurality of electrodes are configured to generate impedance measurements in addition to the cardiac signal measurements, wherein the distal tip circuitry is configured to cause the subset of the plurality of electrodes to switch between generating the impedance measurements and the cardiac signal measurements, wherein the distal tip circuitry is configured to repeatedly receive the cardiac signal measurements from the plurality of electrodes, multiplex the cardiac signal measurements to create a combined signal, and amplify and digitize the combined signal to thereby repeatedly generate a digital signal representing the cardiac signal measurements, wherein the distal tip circuitry is further configured to transmit the impedance measurements and the digital signals to the handle circuitry via the one or more communication elements, wherein the handle circuitry is configured to correlate the impedance measurements with the digital signals and to output the digital signals with the correlated impedance measurements to an external system;

positioning the catheter within a patient's tissue at a particular location to receive digital signals with correlated impedance measurements;

processing the digital signals using the correlated impedance measurements to compute a magnetic heart vector for the tissue at the particular location, the processing including:

computing an impedance vector from the correlated impedance measurements;

deriving, from the digital signals and using the impedance vector, a Poynting energy vector;

computing the magnetic heart vector from the derived Poynting energy vector; and based on the computed magnetic heart vector, generating an indication of whether the tissue at the particular location is scar tissue.

* * * * *